United States Patent [19]

Starrett, Jr. et al.

[11] Patent Number: 5,792,756
[45] Date of Patent: Aug. 11, 1998

[54] PRODRUGS OF PHOSPHONATES

[75] Inventors: John E. Starrett, Jr., Middletown; Muzammil M. Mansuri; John C. Martin, both of Cheshire; David R. Tortolani, Meriden; Joanne J. Bronson, Madison, all of Conn.

[73] Assignees: Institute of Organic Chemistry and Biochemistry of the Academy of Sciences of the Czech Republic, Czech Rep.; Rega Stichting v.z.w., Belgium

[21] Appl. No.: 481,715

[22] Filed: Jun. 7, 1995

Related U.S. Application Data

[62] Division of Ser. No. 320,632, Oct. 11, 1994, Pat. No. 5,663,159, which is a continuation of Ser. No. 153,556, Nov. 16, 1993, abandoned, which is a continuation of Ser. No. 583,906, Sep. 14, 1990, abandoned.

[51] Int. Cl.⁶ .................... C07F 9/02; A61K 31/675
[52] U.S. Cl. .................................... 514/86; 544/243
[58] Field of Search ........................ 544/243; 514/86

[56] References Cited

U.S. PATENT DOCUMENTS

| | | | |
|---|---|---|---|
| 3,929,840 | 12/1975 | Christensen | 260/348 |
| 4,816,447 | 3/1989 | Ashton | 514/81 |
| 4,816,570 | 3/1989 | Farquhar | 536/27 |
| 4,968,788 | 11/1990 | Farquhar | 536/27 |
| 5,032,680 | 7/1991 | Kawai | 536/23 |
| 5,476,938 | 12/1995 | Vemishetti et al. | 544/243 |

FOREIGN PATENT DOCUMENTS

| | | | |
|---|---|---|---|
| 0.253.412 | 1/1988 | European Pat. Off. | C07F 9/65 |
| 0 269 947 B1 | 6/1988 | European Pat. Off. | C07F 9/547 |
| 0.206.459 | 12/1988 | European Pat. Off. | C07F 9/547 |
| 1.135.029 | 11/1968 | United Kingdom . | |

OTHER PUBLICATIONS

Bacon, T.H., "Comparative Activity of Penciclovir Acyclovir Against epstein–Barr Virus," Antiviral Res 23:99 (1994).

Balzarini et al. "Differential Antiherpesvirus and Antiretrovirus Effects of the (S) and (R) Enantiomers of Acyclic Nucleoside Phosphonates," Antimicro AG & Chemo 37(2):332–338 (1993).

Barditch–Crovo et al., "A Randomized, Double–Blind, Placebo–Controlled Phase I/II Evaluation of 9–[–2(bispivaloyloxy–methyl)phosphonyl–methoxy]–adenine (bis–POM PMEA), an Orally Bioavailable Prodrug of the Anti–HIV Nucleotide, PMEA," 8th International Conference on Antiviral Research, Santa Fe, NM Abstract #9;A229 (Apr. 23–28, 1995).

Barditch–Crovo et al., "Copy of Slides of the Abstract #9 Presentation," 8th International Conference on Antiviral Research, Santa Fe, NM 14 pages (Apr. 23–28, 1995).

Beres, "Synthesis and Antitumor and Antiviral Properties of 5–Halo– and 5–(Trifluoromethyl)–2'–deoxyuridine 3',5'–Cyclic Monophosphates and Neutral Triesters," J Med Chem 29:1243–1249 (1986).

Bronson et al., "Synthesis and Antiviral Activity of Phosphonylmethoxyethyl Derivatives of Purine and Pyrimidine Bases," J Am Chem Soc 401:72–87 (1989).

De Clercq, "Broad–Spectrum Anti–DNA Virus and Anti–Retrovirus Activity of Phosphonylmethoxalkylpurines and –Pyrimidines," Biochem Pharm 42(5):963–972 (1991).

Eto, "Specific Effects of 4–Morpholine–N, N'–dicyclohexylcarboxamidine as a Catalyst for the Alkylation and Phosphrorylation of Ribonucleosides by a Two–step Phosphorylating Agent, Mtbo: Its Application to the Synthesis of Cytokinin–like Nucleotides," Biol Chem 55(8):1999 (1991).

Farquhar et al, "Biologically Reversible Phosphate–Protective Groups," J Pharm Sci 72:324–325 (1983).

Farrow et al, "Synthesis and Biological Properties of Novel Phosphotriesters: A New Approach to the Introduction of Biologically Active Nucleotides into Cells," J Med Chem 33:1400–1406 (1990).

Germershausan, "Comparison of the Modes of Antiviral Action of 2'–Nor–deoxyguanosine and its Cyclic Phosphate, 2'–Nor–cyclic GMP," Antimicro AG & Chemo 29:1025 (1986).

Hartmann et al., "In vitro activity of acyclic nucleoside phosphonate derivatives against feline immunodeficiency virus in Crandell feline kidney cells and feline peripheral blood lymphocytes," Antiviral Chem & Chemo 5(1):13–19 (1994).

Holy et al., "Phosphonylmethyl Ethers of Nucleosides and Their Acyclic Anlogues," Nucleotide Analogues 51–71 (1989).

Hoover et al., "Early therapy of feline leukemia virus infection (FeLV–Faids) with 9–(2–phosphonymethoxyethyl)adenine (PMEA)," Antiviral Res 16:77–92 (1991).

Iyer et al., "Synthesis of Acyloxyalkyl Acylphosphonates as Potential Prodrugs of the Antiviral, Trisodium Phosphonoformate (Foscarnet Sodium)," Tet Lett 30(51):7141:7144 (1989).

Kumar et al., "Synthesis and Biological Evaluation of Some Cyclic Phosphoramidate Nucleoside Derivatives," J Med Chem 33:2368–2375 (1990).

MacCoss, "The Synthesis, Characterization, and Preliminary Biological Evaluation of 1–Beta–D–Arabinofuranosylcytosine–5'–Diphosphate–L–1,2–Dipalmitin," Biochem Biophys Res Comm 85:714 (1978).

(List continued on next page.)

*Primary Examiner*—Mukund J. Shah
*Assistant Examiner*—Brenda Coleman
*Attorney, Agent, or Firm*—Max D. Hensley

[57] ABSTRACT

There are disclosed novel oral prodrugs of phosphonate nucleotide analogs which are hydrolyzable under physiological conditions to yield compounds which are useful as antiviral agents, especially as agents effective against RNA and DNA viruses. They may also find use as antitumor agents.

7 Claims, No Drawings

OTHER PUBLICATIONS

Midoux, "Drug Targeting: Anti–HSV–1 Activity of Mannosylated polymer–Bound 9–(2–Phosphonylmethoxyethyl Adenine," Biochem Biophys Res Comm 167(3):1044–1049 (1990).

Naesens, "Pharmacokinetics in Mic of Bis(POM)–PMEA, the Bis(pivaloyloxymethyl) Ester Prodrug of 9–(2–Phosphonylmethoxyethyl)adenine," 8th International Conference on Antiviral Research, Santa Fe, NM Abstract#98:A277 (Apr. 23–28, 1995).

Naesens et al., "Antiviral Efficacy in Mice of Oral Bis–(POM)–PMEA, the Bis(pivaloyloxymethyl) Ester of Prodrug of 9–(2–Phosphonylmethoxyethyl)adenine," 8th International Conference on Antiviral Research, Santa Fe, NM Abstract#96:A229 (Apr. 23–28, 1995).

Naesens et al., "Efficacy of Oral 9–(2–phosphonylmethoxyethyl)–2,6–diaminopurine (PMEDAP) in the Treatment of Retrovirus and Cytomegalovirus Infections in Mice," Journal of Medical Virology 39:167–172 (1993).

Naesens et al., "Single–dose administration of 9–(2–phosphonylmethoxyethy)adenine (PMEA) and 9–(2–phosphonylmethoxyethyl)–2,6diaminopurine (PMEDAP) in the prophylaxis of retrovirus infection in vivo," Antiviral Res 16:53–64 (1991).

Rosenberg et al. "Phosphonylmethoxyalkyl and Phosphonylalkyl Derivatives of Adenine," Collect Czech Chem Commun 53:2753–2777 (1988).

Rosenberg et al, "Synthesis of Potential Prodrugs and Matebolites of 9–(S)–(3–Hydroxy–2–Phosphonylmethoxypropyl)Adenines," Collect Czech Chem Commun 52:2792–2800 (1987).

Snoeck et al, "Antiviral activity of anti–cytomegalovirus agents (HPMPC, HPMPA) assessed by a flow cytometric method and DNA hybridization technique," Antiviral Res 16:1–9 (1991).

Snoeck et al, "New Acyclic nucleoside phosphonate derivatives as inhibitors of human cytomegalovirus," 29th Interscience Conference on Antimicrobial Agents and Chemotherapy p. 327, Abstract No. 1334 (Sep. 17–20, 1989).

Spadari, "Antivirals based on Inhibition of Herpesvirus Thymidine Kinases," Drug News and Perspective 2:333 (1989).

Srivastva et al. "Bioreversible Phosphate Protective Groups: Synthesis and Stability of Model Acyloxymethyl Phosphates," Bioorg chem 12:118–129 (1984).

Starrett et al, "Synthesis and in vitro evaluation of a phosphonate prodrug: bis(pivaloyloxymethyl) 9–(2–phosphonylmethoxyethyl)adenine," Antiviral Res 19:267–273 (1992).

Starrett et al., "Synthesis, Oral Bioavailability Determination, and in Vitro Evaluation of Prodrugs of the Antiviral Agent 9–[2–(Phosphonomethoxy)eth]adenine (PMEA)," J Med Chem 37:1857–1864 (1994).

Vahlenkamp et al., "(R)–9–(2– Phosphonylmethoxypropyl)–2,6–Diaminopurine Is a Potent Inhibitor of Feline Immunodeficiency Virus Infection," Antimicro AG & Chemo 39(3):746–749 (1955).

Yokota et al, "Inhibitory effects of acyclic nucleoside phosphonate analogues on hepatitis B virus DNA synthesis in HB611 cells," Antiviral Chem & Chemo 5(2):57–63 (1994).

Yokota et al., Antiviral Chemistry and Chemotherapy 5(2): 57–63, Mar. 1994.

PRODRUGS OF PHOSPHONATES

This is a divisional of application Ser. No. 08/320,632 filed on Oct. 11, 1994, U.S. Pat. No. 5,663,159 which is a continuation of U.S. application Ser. No. 08/153,556, filed Nov. 16, 1993, now abandoned, which is a continuation of U.S. application Ser. No. 07/583,906, filed Sep. 14, 1990, now abandoned.

BACKGROUND OF THE INVENTION

1. Field of the Invention

The present invention relates to novel orally active prodrugs of phosphonate nucleotide analogs, their pharmaceutically acceptable acid addition salts, a process for their production, and to their use. The prodrugs of the present invention exhibit antitumor activity and a broad spectrum of antiviral activity.

2. Description of the Prior Art

Infectious viral diseases are recognized as an important medical problem. Progress against infectious viral diseases requires the development of drugs with selective antiviral activity while remaining benign to normal cell lines. Among the antiviral agents currently under study, which seem to possess selectivity, are phosphonate nucleotide analogs. In general, these compounds are structural analogs of the monophosphates nucleoside analogs.

A number of phosphonate nucleoside analogs have been described in the literature. These nucleoside analogs have been described as potent and selective antiviral agents with activity against a broad spectrum of DNA and RNA viruses.

For example, 9-(3-hydroxy-2-phosphonylmethoxypropyl (HPMP) and (2-phosphonylmethoxy)ethyl (PME) analogs of purine (adenine (A), guanine (G), 2,6-diaminopurine (DAP), 2-monoaminopurine (MAP), hypoxanthine (Hx) and pyrimidine (cytosine (C), uracil (U), thymine (T) were evaluated for antiviral properties. (S)-HPMPA, (S)-cyclic HPMPA, (S)-HPMPC, (S)-HPMPG, (S)-HPMPDAP, PMEDAP, PMEG and PMEA were active against herpes simplex virus, type 1 and 2 (HSV-1 and -2). (S)-HPMPA and (S)-cyclic HPMPA were active against varicella zoster virus (VZV). (S)-HPMPC was active against human cytomegalovirus (HCMV), a common cause of opportunistic infection in AIDS patients. (S)-HPMPA and (S)-cyclic HPMPA are active against adenovirus and vaccinia virus. PMEA, PMEDAP, and PMEMAP are active against human immunodeficiency virus (HIV), the human retrovirus responsible for AIDS. De Clercq, et al, *Antiviral Research*, 8: 261–272 (1987).

Bronson, et al., report on the series of acyclic nucleotide analogs having a common PME side chain attached to a purine or pyrimidine base which were prepared and selected for in vivo antiviral activity against retroviruses and herpes viruses. The adenine analog, PMEA, showed good in vitro activity against HIV and Rauscher murine leukemia virus (R-MuLV), and was more potent in vivo than 3'-azido-3'-deoxythymidine (AZT) in the treatment of R-MuLV in mice. PMEA also had a significant antiviral effect in vivo against murine cytomegalovirus (MCMV), and in vitro activity against HCMV. The guanine analog, PMEG, was exceptionally potent in vitro against herpes viruses. In vivo, PMEG was >50-fold more potent than acyclovir against HSV 1 infection in mice. *Nucleotide Analoas as Antiviral Agents*; ACS Symposium Series 401; Martin, J. C. Ed.: Washington, D.C., 1989, Chapter 5, pp. 72–87. Kim, et al., in *J. Med. Chem.*, 33: 1207–1213 (1990), describe a similar series of compounds.

De Clercq, et al, in *Nature*, 323: 464–467 (1986) state that (S)-HPMPA has potent and selective activity against a broad spectrum of DNA viruses, including HSV-1 and 2, VZV, thymidine kinase-deficient (TK$^-$) mutants of herpes simplex HCMV, phocid herpesvirus type 1 (seal herpesvirus, SeHV), the simian herpesvirus platyrrhinae (HVP), suid herpesvirus type 1 (SHV-1, or pseudorabies virus or Aujeszky's disease virus), bovid herpesvirus type 1 (infectious bovine rhinotracheitis virus, BHV-1), equid herpesviruse type 1 (equine abortion virus, EHV-1), African swine fever (ASF) virus, vaccinia virus; and human adenoviruses, and retroviruses such as murine sarcoma virus (MSV). It is also reported that, in mice and rabbits in vivo, the compound is effective against both local and systemic infections with herpes simplex virus type 1, including herpetic keratitis caused by a TK$^-$ mutant which is resistant to the classical anti-herpes drugs.

European Patent Application 205,826, to De Clercq, et al, published Dec. 30, 1986, discloses that HPMPA analogs are active against Moloney mouse sarcoma virus, and are expected to be effective against retroviruses in general.

Reist and Sturm in PCT/U.S. Pat. No. 84/00737, published Dec. 6, 1984 disclosed new phosphonic acid analogs of nucleoside phosphates which are useful as antivirals for incorporation into viral DNA.

Adenine phosphonic acid analogs and their synthesis are disclosed in the United Kingdom Patent application of Holy, et al., GB 2,134,907A, published on Aug. 22, 1984, and it's related U.S. Pat. No. 4,659,825. A preferred example of one of these compounds, is known as (S)-9-((3-hydroxy-2-phosphonylmethoxy)propyl)adenine (HPMPA). HPMPA was disclosed by E. DeClercq, et al., in *Nature*, 323: 464–467, (1986), in *Antiviral Research*, 8: 261–272, (1987), and earlier by A. Holy, et al., *Nucleic Acids Research*, Symposium Series No. 14: 277–278, (1984).

Phosphonylmethoxyalkylpurine analogs have also been evaluated for their antitumor activity in murine tumor models. HPMPA, PMEA, and PMEG were found to be active against intraperitoneal P388 leukemia. PMEG was also found to be active against B16 melanoma. Rose, et al, *J. of the Nat. Cancer Inst.*, Vol. 82, No. 6 (1990).

A problem with nucleotides and other ionic organophosphate esters is their inability to traverse biological membranes. Liebman, et al, *J. Biol. Chem.*, 216: 823 (1955); Roll, et al, *J. Biol. Chem.*, 220: 439 (1956). These compounds must, therefore, be given parenterally in order to achieve adequate serum levels to exert an antiviral effect.

Parenteral treatment is highly undesirable, especially with HIV infected patients. With HIV infected patients oral treatment is preferred since (i) HIV infected patients are very ill and need to be on chronic chemotherapy programs to maintain their health; (ii) the risk of using needle stick and presence of blood is high for health workers; (iii) disposal of infected needles is a problem; and (iv) the need for long-term maintenance therapy.

The inventors of this invention have carried out studies in order to circumvent the above-mentioned problem. The present application, thus, relates to the preparation and use of a number of oral prodrugs of phosphonate nucleotide analogs.

In *J. Med. Chem.*, 32:1457–1463 (1989), Bronson et al., disclose the synthesis of HPMPC wherein the following compound is disclosed as an intermediate In *Nucleotide Analogs as Antiviral Agents*, ACS Symposium Series 401, J. C. Martin, Ed., p. 72, American Chemical Society, Washington, D.C. (1989), Bronson et al., disclose the synthesis of phosphonylmethoxy ether derivatives wherein the following compound was disclosed as an intermediate wherein R is ethyl or isopropyl.

European Patent Application EP-270,885 of Webb, et al., published Jun. 15, 1988 discloses a process for the preparation of purin-9-ylalkylenoxymethyl phosphonic acids, wherein several intermediates are produced in the practice of the process. One such intermediate is dialkylphosphonylmethyl which has the general structural formula wherein $R^1$ and $R^2$, independently, are selected from $C_{1-6}$ alkyl.

European Patent Application EP 253,412 of Holy, et al., published Jan. 20, 1988, discloses the preparation of a series of N-phosphonylmethoxyalkyl derivatives of pyrimidine and purine bases exhibiting antiviral activitie, wherein in the practice of the process, several intermediates are produced. One such intermediate has the general structural formula European Patent Application EP-269,947 of R. R. Webb, II, et al., published on Jun. 8, 1988, discloses a series antiviral agents which are phosphonomethoxyalkylene purine and pyrimidine derivatives having the following general structure wherein $R^3$ and $R^4$ are independently selected from hydrogen, $C_{1-16}$ alkyl, phenyl and phenyl-$C_{1-4}$-alkylene.

The art compounds are generally distinguished from the compounds of the instant invention by the nature of the groups attached to the phosphorous atom There is no disclosure or suggestion in the above references, or combination thereof, which would make obvious the use of a suitably protected phosphonate derivative prodrug for oral use.

SUMMARY OF THE INVENTION

This invention relates novel prodrugs of phosphonate nucleotide analogs which exhibit antitumor activity and a broad spectrum of antiviral activity and some of which may be used orally. The compounds of the present invention may be represented by the general formula (I):

FORMULA I wherein

B represents adenine (A), cytosine (C), guanine (G), thymine (T), Uracil (U), 2,6-diamino purine (DAP), hypoxanthine (Hx), or Z;

$R^1$ and $R^2$ are identical or different and independently of one another are each $OR^4$, $NH_2$, $NHR^5$, or $N(R^5)_2$; in some cases, $R^1$ and $R^2$ are linked with each other to form a cyclic group, in other cases, $R^1$ or $R^2$ is linked to $R^3$ to form a cyclic group;

$R^3$ represents $C_1$–$C_{20}$ alkyl which may be substituted or unsubstituted by substituents independently selected from the group consisting of hydroxy, oxygen, nitrogen and halogen; when $R^3$ is $CH(CH_2OR^6)CH_2$, $R^1$ and $R^2$ each independently represent OH, and $R^6$ is a hydrolyzable ester group;

$R^4$ represents a physiologically hydrolyzable ester group such as $CH_2C(O)NR^5_2$, $CH_2C(O)OR^5$, $CH_2OC(O)R^5$, $CH(R^5)OC(O)R^5$ (R, S, or RS stereochemistry), $CH_2C(R^5)_2CH_2OH$, or $CH_2OR^5$; $R^4$ may also be $R^{5'}$ provided that $R^4$ and $R^{5'}$ are not simultaneously alkyl;

$R^5$ represents $C_1$–$C_{20}$ alkyl, aryl or aryl-alkyl which may be substituted or unsubstituted by substituents independently selected from the group consisting of hydroxy, oxygen, nitrogen and halogen;

$R^{5'}$ represents $C_4$–$C_{20}$ alkyl, aryl or aryl-alkyl which may be substituted or unsubstituted by substituents independently selected from the group consisting of hydroxy, oxygen, nitrogen and halogen; and Z is independently chosen from Q is independently chosen from H, Cl, NHR$^5$, NR$^5{}_2$, NHC(O)R$^5$, N(C(O)R$^5$)$_2$, OH or NCHN(R$^5$)$_2$.

Also included within the scope of the invention are the pharmaceutically acceptable acid addition salts, the metal salts and the solvate of the compounds of Formula I which may exist in various tautomeric forms.

In another aspect, the application relates to a process for the preparation of the compounds of Formula I.

In yet another aspect, the application relates to the use the compounds of Formula I as a method for the treatment of viral infections in a mammal, which comprises administering an effective non-toxic dose of at least one compound of Formula I.

Another aspect of the application relates to the use of the compounds of Formula I as a method for inhibiting growth of a tumor in a mammal bearing a tumor which comprises administering an effective non-toxic dose of at least one compound of Formula I.

DETAILED DESCRIPTION OF THE INVENTION

This invention relates novel prodrugs of phosphonate nucleotide analogs which exhibit broad spectrum of antiviral activity, some of which may be used orally. The compounds of the instant invention comprise a diester-phosphonate link to nucleoside analogs of pyrimidine and purine bases. More particularly, it relates to compounds of the general structural formula as shown in Formula I

FORMULA I wherein

B represents adenine (A), cytosine (C), guanine (G), thymine (T), Uracil (U), 2,6-diamino purine (DAP), hypoxanthine (Hx), or Z;

R$^1$ and R$^2$ are identical or different and independently of one another are each OR$^4$, NH$_2$, NHR$^5$, or N(R$^5$)$_2$; in some cases, R$^1$ and R$^2$ are linked with each other to form a cyclic group, in other cases, R$^1$ or R$^2$ is linked to R$^3$ to form a cyclic group;

R$^3$ represents C$_1$–C$_{20}$ alkyl which may be substituted or unsubstituted by substituents independently selected from the group consisting of hydroxy, oxygen, nitrogen and halogen; when R$^3$ is CH(CH$_2$OR$^6$)CH$_2$, R$^1$ and R$^2$ each independently represent OH, and R$^6$ is a hydrolyzable ester group;

R$^4$ represents a physiologically hydrolyzable ester group such as CH$_2$C(O)NR$^5{}_2$, CH$_2$C(O)OR$^5$, CH$_2$OC(O)R$^5$, CH(R$^5$)OC(O)R$^5$ (R, S, or RS stereochemistry), CH$_2$C(R$^5$)$_2$CH$_2$OH, or CH$_2$OR$^5$; R$^4$ may also be R$^{5\prime}$ provided that R$^4$ and R$^{5\prime}$ are not simultaneously alkyl;

R$^5$ represents C$_1$–C$_{20}$ alkyl, aryl or aryl-alkyl which may be substituted or unsubstituted by substituents independently selected from the group consisting of hydroxy, oxygen, nitrogen and halogen;

R$^{5\prime}$ represents C$_4$–C$_{20}$ alkyl, aryl or aryl-alkyl which may be substituted or unsubstituted by substituents independently selected from the group consisting of hydroxy, oxygen, nitrogen and halogen; and Z is independently chosen from

Q is independently chosen from H, Cl, NHR$^5$, NR$^5{}_2$, NHC(O)R$^5$, N(C(O)R$^5$)$_2$, OH or NCHN(R$^5$)$_2$.

The compounds of Formula I are prodrugs of phosphonate nucleotides and have the same utility as the known or parent nucleotide analog. Thus the compounds of Formula I are useful as antiviral and antitumor agents.

The novel compounds of the present invention provide marked advantages over known nucleotides or analogs thereof in that these novel compounds are orally active.

The most preferred compounds of the invention are listed below, and experimental details for their preparation and characterization follow. Those which are not shown by specific example are readily prepared by analogous procedures.

A preferred example of the compounds of the instant invention are the compounds having the general structural formula as shown in Formula (II):

FORMULA II wherein

B, R$^1$ and R$^2$ are as described in Formula I, provided that when Q is NCHN(R$^5$)$_2$, then R$^5$ is not CH$_3$;

X represents hydrogen, methyl, CH$_2$OR$^6$ (R;S; or RS stereochemistry), hydroxymethyl or substituted or unsubstituted lower alkyl; when X is CH$_2$OR$^6$, R$^1$ and R$^2$, may additionally be independently chosen from OH; and R$^6$ is a hydrolyzable group; provided that when X is CH$_2$OR$^6$, R$^6$ is not CH$_2$Ph, and R$^1$ and R$^2$ are not both ethoxy; further, when R$^1$ is methoxy and R$^2$ is hydrogen, R$^6$ is not methyl; and further provided that when R$^1$ is methoxy and R$^2$ is hydrogen, R$^6$ is not octyl.

Another preferred example of the compounds of the instant invention are the compounds having the general structural formula as shown in Formula (III):

FORMULA III wherein

B, and R$^1$ are as previously described in Formula I;

X is as described in Formula II;

R$^7$ represents OH, NH$_2$, NHR$^5$, or NR$^5{}_2$; and

R$^5$ is as described in Formula I.

Still another preferred example of the compounds of the instant invention are the compounds having the general structural formula as shown in Formula (IV):

FORMULA IV wherein $R^8$ and $R^9$ are identical or different and independently of one another are each $NR^{12}$, or oxygen;

$R^{10}$ and $R^{11}$ are identical or different and independently of one another are each hydrogen, or $R^5$;

$R^{12}$ represents hydrogen or a lower alkyl;

m and n are identical or different and independently of one another are each 0 or 1;

B and $R^5$ are as described in Formula I; and

X is as described in Formula II.

Yet another preferred example of the compounds of the instant invention are the compounds having the general structural formula as shown in Formula V

FORMULA V

*stereochemistry is R, S, or RS wherein $R^{13}$ represents $OR^4$, $NHR^5$, $NR^5{}_2$, or OH, provided that $R^{13}$ is not OH when B is A or C; and B, $R^4$ and $R^5$ are as described in Formula I.

The term "$C_1$ to $C_{20}$ alkyl" as used herein and in the claims (unless the context indicates otherwise) means saturated or unsaturated, branched or straight chain hydrocarbon group having 1 to 20 carbon atoms such as methyl, ethyl, propyl, isopropyl, butyl, isobutyl, t-butyl, etc. Unless otherwise specified in the particular instance, the term "substituted or unsubstituted" as used herein and in the claims is intended to mean hydrocarbon group wherein an atom, element or group is regarded as having replaced a hydrogen atom, said substituted alkyl groups are preferably substituted with a member selected from the group consisting of hydroxy, oxygen, nitrogen and halogen.

The term "prodrug" as used herein and in the claims (unless the context indicates otherwise) denotes a derivative of an active drug which is converted after administration back to the active drug. More particularly, it refers to derivatives of nucleotide phosphonates antiviral drugs which are capable of undergoing hydrolysis of the ester moiety or oxidative cleavage of the ester or amide moiety so as to release active, free drug. The physiologically hydrolyzable groups serve as prodrugs by being hydrolyzed in the body to yield the parent drug per se, and thus, the prodrugs of the present invention are preferably administered orally.

Synthesis of the phosphonate nucleotide analoas

The phosphonate nucleotide analogs are known compounds and therefore, the compounds as such and their chemical synthesis are not a part of the present invention. The synthesis of a number of phosphonate nucleotide analogs have been described in the literature.

For example, the synthesis of the phosphonates PMEA is disclosed in Holy and Rosenberg, Collect. Czech. Chem. Commun., 52:2801, (1987), and Bronson, et al, Nucleotide Analogues as Antiviral Agents, ACS Symposium Series 401, J. C. Martin, Ed., p. 72, American Chemical Society, Washington, D.C. (1989).

Bronson, et al, J. Med. Chem., 32: 1457–1463 (1989) discloses the preparation of HPMPC from (R-)-2,3-O-isopropylideneglycerol.

European Patent Application 253,412, published Jan. 20, 1988 to Holy, et al, discloses methods for the preparation of PME and HPMP analogs of pyrimidine and purine bases.

Recently Holy et al Collect. Czech. Chem. Commun., 54: 2190–2210 (1989), described the preparation of N-(2-phosphonylmethoxy-ethyl) ("PME") analogs of purine and pyrimidine bases, as analogs of the antiviral 9-(2-phosphonylmethoxyethyl)adenine ("PMEA). The synthesis consists of alkylation of alkali metal salts of heterocyclic bases or their N- or O-substituted analogs with diethyl 2-p-toluenesulfonyloxyethyoxymethylphosphonate, 2-chloroethyoxymethylphosphonate, or 2-bromoethyoxymethylphosphonate. The obtained N-(2-diethyoxyphosphonylmethoxyethyl) analogs of heterocyclic bases were treated with bromotrimethylsilane to give phosphonic acids. The phosphonic acids were prepared from pyrimidines (uracil, cytosine and their 5-methyl analogs), purines (adenine and its N-$^6$ and C(2)-substituted analogs, hypoxanthine, guanine, 6-hydrazinopurine and 6-methylthiopurine etc.) and their analogs (3-deazaadenine etc.).

The synthesis of HPMPA is disclosed in Holy, Rosenberg, and Dvorakova, Collect. Czech. Chem. Commun. 54:2190 (1989).

Synthesis of dialkyl phosphonates

Quast, et al, Synthesis 490 (1974), has shown that dichlorophosphonates can be prepared by reacting phosphonates with $PCl_5$:

Moedritzer, K. CA 82, 86340, has shown that dichlorophosphonates can be prepared by reacting dimethylphosphonates with thionyl chloride.

Stowell, et al, (Tetrahedron Lett., 3261, (1990)) has shown that dichlorophosphonates can be reacted with alcohols or amines to give dialkylesters or dialkylamides:

The substituted phosphonates of the present invention were prepared by several methods: 1) Reaction of the phosphonate with thionyl chloride to give the dichlorophosphonate which was reacted further to give the disubstituted phosphonate:

2) Mono substituted phosphonates were obtained by the basic hydrolysis of the disubstituted phosphonate:

3) The monosubstituted phosphonates were chlorinated as before and reacted with a different alcohol or amine to give variably substituted phosphonates:

4) Diacyloxyalkyl phosphonates were obtained by reaction of the unsubstituted phosphonate with a substituted chloromethyl ether:

PROTOCOL FOR DETERMINING ORAL BIOAVAILABILITY OF PRODRUGS

Groups of rats, 3 rats per group, were given a single iv dose of 30 mg/kg of PMEA or a single oral dose of 30 mg-equiv/kg of PMEA or PMEA prodrug. Urine was collected in 0–24 hr and 24–48 hr intervals and analyzed for concentration of PMEA. The bioavailability of PMEA based on urinary excretion data and the bioavailability of PMEA when given as a prodrug was determined. The results are summarized below.

| ORAL BIOAVAILABILITY OF SELECTED PMEA PRODRUGS IN RATS | |
|---|---|
| COMPOUND OF EXAMPLE NO. | ABSOLUTE BIOAVAILABILITY |
| 1 (PMEA) | 7.8 |
| 9 | 17.0 |
| 12 | 15.4 |
| 13 | 14.6 |
| 14 | 34.9** |
| 15 | 6.5 |
| 16 | 14.2 |
| 22 | 16.2 |
| 34 | 14.0 |
| 35 | 11.1 |

**DETECTED AS THE MONOETHYL ESTER

| IN VITRO ACTIVITY OF SELECTED PMEA PRODRUGS AGAINST HSV-2 (G STRAIN) | | |
|---|---|---|
| COMPOUND OF EXAMPLE NO. | $ID_{50}$ (μg/mL)* | TOXICITY (μg/mL) |
| 1 (PMEA) | 39 | >166 |
| 9 | 0.28 | 100 |
| 12 | 0.17 | 100 |
| 13 | <0.1 | 100 |
| 14 | 3.3 | 100 |
| 15 | 8.1 | 100 |
| 16 | >100 | 100 |
| 22 | 110 | >166 |
| 34 | 42 | >166 |
| 35 | 34 | >166 |

*DOSE WHICH GIVES A 50% REDUCTION OF PLACQUE FORMATION

The compounds of Formula I may be formulated for oral or parenteral use in a conventional manner using known pharmaceutical carriers and excipients, and they may be presented in unit dosage form or in multiple dose containers. The compositions may be in the form of tablets, capsules, solutions, suspensions or emulsions. These compounds may also be formulated as suppositories utilizing conventional suppository bases such as cocoa butter or other fatty materials. The compounds may, if desired, be administered in combination with other antiviral antibiotics.

When provided in unit dosage forms, the compositions may contain from about 0.1 to about 100 mg/kg/dose of the active ingredient of Formula I. The dosage of the compounds of Formula I is dependent on such factors as the weight and age of the patient, as well as the particular nature and severity of the disease, and within the discretion of the physician. The dosage for adult human treatment may vary depending on the frequency and route of administration.

The following examples are intended for illustrative purpose only and are not to be construed as limiting the invention in sphere or scope. All temperatures are understood to be in degrees in C when not specified. The nuclear magnetic resonance (NMR) spectral characteristics refer to chemical shifts (δ) expressed in parts per million (ppm) versus tetramethylsilane (TMS) as reference standard.

Except where otherwise noted, $^1$H spectra were recorded at 300 MHz and $^{13}$C spectra were recorded at 75 MHz. The relative area reported for the various shifts in the proton NMR spectral data corresponds to the number of hydrogen atoms of a particular functional type in the molecule. NMR assignments are based on the numbering system shown below:

The nature of the shifts as to multiplicity is reported as broad singlets (bs), singlets (s), multiplet (m), doublet (d), doublet of doublets (dd), triplet (t), or quartet (q). Coupling constants are given in hertz. When not specified, abbreviations employed are standard American Chemical Society (ACS) abbreviations as entered on the ACS Style Guide. The infrared (IR) spectral descriptions include only absorption wave numbers ($cm^{-1}$) having functional group identification value. All compounds gave satisfactory elemental analyses, or high resolution mass spectrometry (HRMS).

Figure 1:
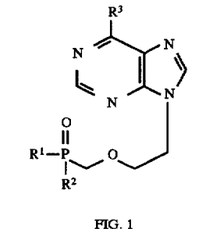
Figures 1, 2:
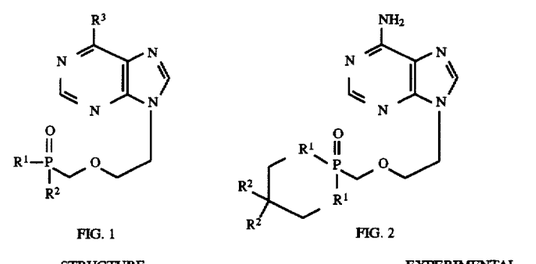
Figure 2:
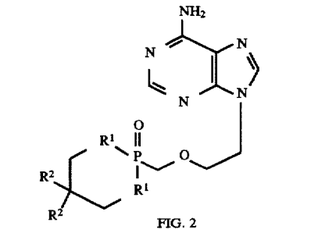

I. General Experimental Methods for Compounds Listed in Table I:

The compounds listed in Table I were synthesized by the corresponding method given at the end of the table. The reaction time, temperature and yield are given in Table I. The structure of the examples corresponds to either FIG. 1 or FIG. 2 given at the top of Table I. Spectral data for all compounds are given in the Examples which follow.

TABLE I

STRUCTURES AND EXPERIMENTAL DATA FOR PMEA PRODRUGS

FIG. 1

FIG. 2

| | | STRUCTURE | | | EXPERIMENTAL | | |
|---|---|---|---|---|---|---|---|
| Example No. | Fig | R1 | R2 | R3 | Method | Temp °C. | Time (h) | Yield % |
| 2 | 1 | iPrO | =$R^1$ | $NH_2$ | e | | | |
| 3 | 1 | PhO | $CH_3O$ | $NH_2$ | e | | | |
| 4 | 1 | iPrO | HO | OH | e | | | |
| 5 | 1 | iPrO | =$R^1$ | Cl | e | | | |
| 6 | 1 | iPrO | =$R^1$ | H | e | | | |
| 9 | 1 | t-BuC(O)OCH$_2$O | =$R^1$ | $NH_2$ | e | — | — | — |
| 10 | 1 | t-BuC(O)OCH$_2$O | iPrO | $NH_2$ | e | | | |
| 11 | 1 | $(CH_3)_3N(+)(CH_2)_2O$ | O$^-$ | $NH_2$ | e | — | — | — |
| 12 | 1 | EtC(O)OCH$_2$O | =$R^1$ | $NH_2$ | e | | | |
| 13 | 1 | iPrC(O)OCH$_2$O | =$R^1$ | $NH_2$ | e | | | |
| 14 | 1 | tBuC(O)OCH$_2$O | $CH_3CH_2O$ | $NH_2$ | e | | | |
| 15 | 1 | tBuC(O)OCH$_2$O | OH | $NH_2$ | e | | | |
| 16 | 1 | iPrO | PhO | $NH_2$ | e | | | |
| 17 | 1 | t-BuC(O)OCH$_2$O | Et$_2$NC(O)CH$_2$O | $NH_2$ | e | | | |
| 18 | 2 | O | H | $NH_2$ | C$^b$ | 22 | 16 | |
| 19 | 1 | Et$_2$N | =$R^1$ | $NH_2$ | C | 22 | 16 | 18 |
| 20 | 1 | iPrO | O$^-$ | $NH_2$ | B | 60 | 24 | 75 |
| 21 | 2 | O | $CH_3$ | $NH_2$ | C | 40 | 24 | 56 |
| 22 | 1 | HO(CH$_2$)$_3$O | O$^-$ | $NH_2$ | B | 60 | 2 | 50 |
| 23 | 1 | CH$_3$(CH$_2$)$_7$O | HO | $NH_2$ | E | 70 | 16 | 29 |
| 24 | 1 | CH$_3$O | =$R^1$ | $NH_2$ | A | 65 | 4 | 47 |
| 25 | 1 | CH$_3$O | O$^-$ | $NH_2$ | B | 60 | 2 | 78 |
| 26 | 1 | H$_2$NCH$_2$C(CH$_3$)$_2$CH$_2$NH— | HO | $NH_2$ | B | 60 | 1.5 | 61 |
| 27 | 1 | HOCH$_2$C(CH$_3$)$_2$CH$_2$O | HO | $NH_2$ | D | 60 | 1.5 | 80 |
| 28 | 2 | NH | CH$_3$ | $NH_2$ | C | 40 | 24 | 46 |
| 29 | 2 | NCH$_3$ | H | $NH_2$ | F | 82 | 24 | 27 |
| 30 | 1 | Et$_2$NC(O)CH$_2$O | O$^-$ | $NH_2$ | F;D$^{a,d}$ | 0;22 | 20;0.3 | 19 |
| 31 | 1 | HOC(O)CH$_2$O | HO | $NH_2$ | D | 22 | 0.1 | 66 |
| 32 | 1 | BuOC(O)CH$_2$O | =$R^1$ | $NH_2$ | F | 82 | 1 | 44 |
| 33 | 1 | EtOC(O)CH$_2$O | =$R^1$ | $NH_2$ | F | 82 | 2 | 51 |
| 34 | 1 | PhO | O$^-$ | $NH_2$ | D | 22 | 1 | 76 |
| 35 | 1 | PhO | =$R^1$ | $NH_2$ | F | 22 | 20 | 38 |
| 36 | 1 | iPr$_2$NC(O)CH$_2$O | O$^1$ | $NH_2$ | F,D$^{a,d}$ | 22;22 | 0.8;0.3 | 8 |
| 37 | 1 | pNO$_2$PhCH$_2$O | =$R^1$ | $NH_2$ | F | 82 | 1 | 15 |
| 38 | 1 | pNO$_2$PhCH$_2$O | O$^-$ | $NH_2$ | D | 60 | 20 | 78 |
| 39 | 1 | CCl$_3$CH$_2$O | =$R^1$ | $NH_2$ | F | 82 | 20 | 44 |
| 40 | 1 | CCl$_3$CH$_2$O | HO | $NH_2$ | D | 60 | 1 | 69 |
| 41 | 1 | PhC(O)OCH$_2$O | =$R^1$ | $NH_2$ | e | 22 | 20 | 9 |
| 42 | 1 | pCF$_3$PhCH$_2$O | =$R^1$ | $NH_2$ | F | 82 | 3 | 15 |

TABLE I-continued

STRUCTURES AND EXPERIMENTAL DATA FOR PMEA PRODRUGS

FIG. 1

FIG. 2

| | | STRUCTURE | | | EXPERIMENTAL | | |
|---|---|---|---|---|---|---|---|
| Example No. | Fig | R1 | R2 | R3 | Method | Temp °C. | Time (h) | Yield % |
| 43 | 1 | HOCH$_2$CF$_2$CH$_2$O | HO | NH$_2$ | F;D[a,d] | 82;22 | 1;1 | 18 |
| 44 | 1 | pCF$_3$PhCH$_2$O | HO | NH$_2$ | D | 60 | 20 | 82 |
| 45 | 1 | CH$_3$(CH$_2$)$_3$NH | =R$^1$ | NH$_2$ | F | 82 | 20 | 27 |
| 46 | 1 | (CH$_3$)$_2$CHCH$_2$O | =R$^1$ | NH$_2$ | A | 60 | 3 | 75 |
| 47 | 1 | (CH$_3$)$_2$CH(CH$_2$)$_2$O | =R$^1$ | NH$_2$ | A | 80 | 1.5 | 77 |

[a]The crude product obtained from method F was employed directly in method D. Temperature and time are given for methods F and D, respectively.
[b]The impure product obtained from column chromatography was recrystallized from 25% MeOH/CH$_3$CN.
[c]The impure product obtained from column chromatography was recrystallized from CH$_3$CN.
[d]See detailed experimental section for synthesis of hydroyxacetamides and difluoroalcohol.
[e]Where no method is given, see detailed experimental section for specific examples.

METHOD OF SYNTHESIS FOR THE COMPOUNDS OF TABLE 1

A: A suspension of 1.00 g (3.66 mmol) of PMEA (1) in 50 mL of thionyl chloride was refluxed for 1 h (see eq. 1). The homogeneous, orange-red solution was cooled and the solvents were removed in vacuo to afford crude dichlorophosphonate 2. The dichloride was taken up in alcohol or amine 3 and stirred at the temperature and the time given in Table I. After cooling the reaction to room temperature the solvents were removed in vacuo. The residue was purified on a 30 mm flash chromatography column, eluting with 10% MeOH/CH$_2$Cl$_2$ to afford 4. (See eq. I)

(eq. 1)

B: An aqueous suspension of 4 was treated with 4 equivalents of NaOH for the time and temperature given in Table I (see eq. 2). The mixture was cooled to room temperature and acidified until pH 8. The majority of the solvent was evaporated and the residue was purified on a C-18 silica gel column, eluting with a gradient of 0–25% MeOH/H$_2$O. The fractions containing the product were combined and evaporated to give 5. (See eq. 2)

(eq. 2)

C: This reaction was performed similarly to method A, except crude dichlorophosphonate 2 was suspended in 30 mL of methylene chloride before adding alcohol or amine 3 (see equation 1).

D: This reaction was performed similarly to method B, except after cooling to room temperature, the reaction was acidified to pH 1.5. (See equation 2).

E: This reaction was run similarly to method B, except after cooling to room temperature the reaction was suspended in 20 mL of water. The mixture was acidified until pH approximately 3–4. The resulting solid was collected and washed with water. The filtrate was cooled to 0° C. and the resulting solid was collected and washed with cold water. The solids were combined and dried overnight at 0.005 mm to afford 106 mg (0.23 mmol) of monooctyl-PMEA.

F: This reaction was performed similarly to method A, except crude dichlorophosphonate 2 was suspended in 30 mL of acetonitrile before adding alcohol or amine 3 (see equation 1).

SPECIFIC EXPERIMENTAL METHODS FOR COMPOUNDS LISTED IN TABLE L

Example 1

Synthesis of 9-(2-Phosphonylmethoxy)ethyladenine (PMEA).

A solution of PMEA diisopropyl ester (75.5 g, 0.21 mol) in 800 mL of anhydrous acetonitrile was treated with bromotrimethylsilane (258 g, 1.69 mol). The resulting clear, yellow solution was stirred at room temperature under argon for about 16 hours. The reaction mixture was concentrated in vacuo and the yellow residue was placed under high vacuum for about 5 hours. 400 mL of water was added next, causing immediate formation of a white precipitate. 500 mL of acetone was added and the pale yellow slurry was stirred at room temperature for about 14 hours. The solid was collected by filtration, washing twice with 150 mL of acetone and once with 150 mL of anhydrous ether. An additional portion of solid was collected from the filtrate to provide a total of 55.0 g (90%) of PMEA as an off-white crystalline solid.

m.p.>250° C.; $UV_{max}$ ($H_2O$) 208 nm ($\epsilon$=19,600) 260 nm ($\epsilon$=14,100); $UV_{max}$ (0.1N HCl) 210 nm ($\epsilon$=19,000) 260 NM ($\epsilon$=13,700); $UV_{max}$ (0.1N NaOH) 216 nm ($\epsilon$=9,600) 262 nm ($\epsilon$=14,500); $^1$H NMR (DMSO-$d_6$) $\delta$ 8.14 (s, 1 H), 8.13 (s, 1 H), 7.27 (br s, 2 H, $NH_2$), 4.32 (t, J=5, 2 H, H-1'), 3.87 (t, J=5, 2H, H-2'), 3.59 (d, J=9, 2H, H-4'); $^{13}$C NMR (DMSO-$d_6$) $\delta$ 151.10 (c-6), 148.70 (C-2), 146.28 (C-4), 143.80 (C-8), 118.05 (C-5), 69.94 (d, J=10, C-2'), 66.27 (d, J=160, C-4'), 43.15 (C-1').

Example 2
Synthesis of PMEA, diisopropyl ester

A slurry of adenine (21.2 g, 157 mmol), 2-[(diisopropylphosphonyl)methoxy]ethyl methanesulfonate (50.0 g, 157 mmol, prepared according to the procedure described by J. J. Bronson et al, in *J. Med. Chem.*, 32: 1457, (1989)), and cesium carbonate (56.0 g, 173 mmol) in 160 mL of anhydrous DMF was heated to 120° C. in a 3-necked, 500-mL, round-bottomed flask equipped with a mechanical stirrer and argon inlet adapter. The reaction mixture was stirred at 120° C. for about 5 hours and then was allowed to cool to room temperature. Insoluble material was removed by filtration and the filtrate was concentrated in vacuo to give 66 g of a yellow solid. Purification by column chromatography on silica gel (10:1, elute with 3% to 5% to 7% MeOH/$CH_2Cl_2$) provided 33 g of an off-white solid. Recrystallization from ethyl acetate provided 30.1 g (54%) of PMEA, diisopropyl ester as a white solid.

Mp 136°–138° C.; $UV_{max}$ (MeOH) 262 nm ($\epsilon$=14,360); $^1$H NMR (DMSO-$d_6$) $\delta$ 8.15 (s, 1H), 8.09 (s, 1H), 7.21 (br s, exch, 2H, $NH_2$), 4.50 (apparent octet, J=6.5 H, 2H, 2POCH), 4.34 (t, J=5 H, 2H, $NCH_2$), 3.91 (t, J=5 Hz, 2H, $CH_2OCH_2P$), 3.79 (d, J=8 Hz, 2H, $OCH_2P$), 1.18 (d, J=6.5 H, 6H, POCH($CH_3$)$_2$], and 1.13 (d, J=6.5 Hz, 6H, POCH($CH_3$)$_2$]); $^{13}$C NMR (DMSO-$d_6$) $\delta$ 155.86 (C-6), 152.23 (C-2), 149.46 (C-4), 140.90 (C-8), 118.57 (C-5), 70.22 (d, J=10 Hz, POCH), 70.05 (d, J=12 Hz, ($CH_2OCH_2P$), 64.50 (d, J=165 Hz, $OCH_2P$), 42.35 ($NCH_2$), 23.61 [d, J=7 H, POCH($CH_3$)$_2$], and 23.52 [d, J=7 Hz, POCH($CH_3$)$_2$]; mass spectrum (methane DCI), m/e (rel intensity) 358 (MH+, 100), 344 (10), 316 (10); Anal. Calc. for $C_{14}H_{24}N_5O_4P$: C, 47.06; H, 6.77; N, 19.60; Found: C, 47.06; H, 7.04; N, 19.65.

Example 3
Synthesis of PMEA, (monomethyl, monphenyl) ester

The crude residue from the reaction of phenol with dichlorophosphonyl-PMEA (see General Method F) was purified on a flash chromatography column, eluting with 10% MeOH/$CH_2Cl_2$. Two compounds were obtained. PMEA, diphenyl ester eluted first (38%), followed by PMEA, monomethyl, monophenyl ester (16%).

Mp 70°–72° C. $^1$H NMR ($d_6$-DMSO) 8.13 (1H, s, H-8), 8.08 (1H, s, H-2), 7.32 (2H, t, J=8, ArH), 7.20 (2H, s, $NH_2$), 7.17 (1H, t, J=7, ArH), 7.00 (2H, d, J=8.5, ArH), 4.34 (2H, t, J=5, H-1'), 4.02 (2H, dd, J=8.3, H-4'), 3.91 (2H, t, J=5, H-2') 3.67 (3H, d, J=11, $CH_3$). $^{13}$C NMR ($d_6$-DMSO; 90 MHz), 156.20 (C-6), 152.84 (C-2), 150.07 (ArC, d, J=8), 149.85 (C-4), 141.79 (C-8), 130.31, 125.64, 120.77 (ArC), 118.84 (C-5), 70.87 (C-2', d, J=11), 63.53 (C-4', d, J=163), 53.83 ($CH_3$, d, J=8), 43.01 (C-1'. IR (KBr) 3270, 3110, 1670, 1600, 1484. MS (FAB) 364 (M+H, 100); Anal. Calcd for $C_{15}H_{18}N_5O_4P.0._{16}$ $H_2O$: C, 49.20; H, 5.04; N, 19.13; Found: C, 49.51; H, 4.92; N, 18.73.

Example 4

Synthesis of 9-(2-Phosphonylmethoxy) ethylhypoxanthine (PMEHx) monoisopropyl ester.

A solution of 6-chloro-9-(2-phosphonylmethoxy) ethylpurine, diisopropyl ester (1g, 2.65 mmol) in 27 mL of 1N NaOH was heated at reflux for 1 h, cooled to room temperature, acidified to pH 1 with 1N HCl and concentrated in vacuo. The residue was purified by C-18 silica gel column chromatography, eluting with 20% MeOH/$H_2O$ to afford 0.51 g (68%) of the title compound.

Mp 192°–194° C. $^1$H NMR ($d_6$-DMSO) 12.27 (1H, br s, NH), 8.04, 8.02 (2H, 2s, H-2, H-8), 4.39 (1H, septet, J=6, CH($CH_3$)$_2$), 4.30 (2H, t, J=5, H-1'), 3.85 (2H, t, J=5, H-2'), 3.65 (2H, d, J=8.5, H-4'), 1.10 (6H, d, J=6, $CH_3$). $^{13}$C NMR ($D_2O$) 157.57 (C=0), 149.94, 149.72 (C-2, C-4), 143.02 (C-8), 119.94 (C-5), 72.09 (CH($CH_3$)$_2$, d, J=6), 71.70 (C-2', d, J=13), 67.80 (C-4', d, J=160), 47.05 (C-1'), 25.28 ($CH_3$, d, J=4), IR (KBr) 3423, 2979, 1716, 1642, 1587, 1562. MS (FAB) 317 (M+H, 100); Anal. Calcd for $C_{11}H_{17}N_4O_5P.0.4$ $H_2O$: C, 40.95; H, 5.53; N, 17.37; Found: C, 41.19; H, 5.68; N, 17.51.

Example 5
Synthesis of 6-Chloro-9-(2-Phosphonylmethoxy) ethylpurine, diisoproryl ester.

To a rapidly stirred solution of 9.86 g (63.8 mmol) of 6-chloropurine in 350 mL of anhydrous DMF was added 1.91 g (63.8 mmol) of sodium hydride (80% in mineral oil). The heterogeneous mixture was heated at 95° C. for about 20 hours, cooled to room temperature and concentrated in vacuo. The residue was purified by silica gel chromatography, eluting with 5% MeOH/$CH_2Cl_2$ to give 4.53 g of the title compound.

$^1$H NMR ($d_6$-DMSO) 8.76 (1H, s, H-8), 8.63 (1H, s, H-2), 4.82 (2H, t, J=5, H-1'), 4.42 (2H, septet, J=6, CH($CH_3$)$_2$, 3.93 (2H, t, J=5, H-2'), 3.75 (2H, d, J=8, H-4'), 1.11 (6H, d, J=6, $CH_3$), 1.05 (6H, d, J=6, $CH_3$). $^{13}$C NMR ($d_6$-DMSO) 152.44 (C-6), 151.88 (C-2), 149.39 (C-4), 148.13 (C-8), 131.13 (C-5), 70.24 (CH($CH_3$)$_2$, d, J=6), 70.00 (C-2', d, J=11), 64.64 (C-4', d, J=165), 43.43 (C-1'), 23.65 ($CH_3$, d, J=4.5), 23.47 ($CH_3$, d, J=4.5). IR (KBr) 3459, 3077, 2982, 2936, 1564. MS (methane/DCI) 377 (M+H, 100); Anal. Calcd for $C_{14}H_{22}N_4O_4Cl_1P_1$: C, 44.63; H, 5.89; N, 14.87; Found: C, 44.40; H, 5.93; N, 14.53.

Example 6
Synthesis of 9-(2-phosphonylmethoxy)ethylpurine diisopropyl ester.

A solution of 6-Chloro-9-(2-phosphonylmethoxy) ethylpurine, diisopropyl ester (0.94 g, 2.5 mmol) in 20 mL of ethanol/cyclohexene (1:1) was treated with 0.5 g of Pd(OH)$_2$/C. The reaction was stirred at reflux for about 20 hours, diluted with hot ethanol and filtered through celite. The filtrate was concentrated in vacuo and the residue was purified by flash column chromatography, eluting with 10% MeOH/$CH_2Cl_2$ to afford 0.49 g (58%) of the title purine as a clear yellow oil.

¹H NMR (d₆-DMSO) 9.14, 8.92, 8.55 (3H, 3s, H-2, H-6, H-8), 4.47 (2H, t, J=5, H-1'), 4.42 (2H, septet, J=6, CH(CH₃)₂), 3.94 (2H, t, J=5, H-2'), 3.77 (2H, d, J=8, H-4'), 1.12 (6H, d, J=6, CH₃), 1.05 (6H, d, J=6, CH₃). IR 3459, 2982, 2937, 1597, 1581, 1506. MS (methane/DCI) 343 (M+H, 100), 329 (12), 301 (50); Anal. Calcd for $C_{14}H_{23}N_4O_4P \cdot 0.25\ H_2O$: C, 48.50; H, 6.83; N, 16.16; Found: C, 48.55; H, 6.71; N, 15.88.

Example 7
Synthesis of hydroxyacetamides necessary for preparation of Example 21 and Example 27.

(a) 2-hydroxy-N-N-diethylacetamide

A solution of 10.5 g (0.0702 mol) of 2-chloro-N-N-diethylacetamide in 35 mL of glacial acetic acid was refluxed for about 16 hours. The solvents were removed in vacuo, the last traces of acetic acid being azeotropically removed with toluene. The residue was dissolved in 125 mL of methanol and treated with 10.85 g (0.20 mol) of sodium methoxide. The reaction was stirred for about 3 hours and neutralized with Dowex 50X8-200 acidic ion exchange resin. The solvents were removed in vacuo and the residue was purified on a flash chromatography column, eluting with hexane/ethyl acetate 1:1 to give 6.75 g (73%) of 2-hydroxy-N-N-diethyl- acetamide.

(b) 2-hydroxy-N-N-diisopropylacetamide

To a solution of 44.5 g (0.44 mol) of N-N-diisopropyl amine in 125 mL of hexane cooled to -78° C. was added dropwise 17.6 mL (0.22 mol) of chloroacetyl chloride. After completion of the addition, the cooling bath was removed and stirring was continued for about 30 minutes. The isopropylammonium chloride was removed by filtration through celite and the filtrate was stripped to give 30.5 g (77%) of 2-chloro-N-N-diisopropylacetamide. Hydrolysis of this compound as described above afforded a 45% yield of 2-hydroxy-N-N-diisopropylacetamide.

Example 8
Synthesis of the difluoroalcohol necessary for the preparation-of Example 34.

(a) 2,2-Difluoro-3-hydroxy-propan-1-ol

A solution of 9.07 g (0.0521 mol) of 1,3-diacetyl acetone in 20 mL of DAST was stirred at 22° C. for 2 days, diluted with ethyl acetate, washed with saturated NaHCO₃ and water, then dried over Na₂SO₄ and concentrated to yield 9.54 g of 1,3-diacetyl-2,2- difluoropropane. The diacetyldifluoropropane (7.53 g, 38.4 mmol) was dissolved in 300 mL of methanol and treated with 6.45 g (119 mmol) of sodium methoxide. After stirring at 22° C. for about 2.5 hours, the reaction was neutralized with Dowex 50X8-200 acidic ion exchange resin, filtered and stripped to give 3.7 g (86%) of the title compound.

Example 9
Synthesis of PMEA, di(pivaloyloxymethyl ester)

To a rapidly stirred solution of 1.00 g (3.66 mmol) of PMEA in 15 ml of anhydrous DMF was added 2.08 g (7.32 mmol) of N,N'-dicyclohexyl-4-morpholine carboxamidine and 2.75 g (18.33 mmol) of chloromethyl pivalate. The heterogeneous mixture became homogeneous after about 15 minutes and was then allowed to stir at 22° C. for about 36 hours. The insolubles were filtered off and the filtrate was concentrated in vacuo. The residue was then partitioned between (50 ml) water and (50 ml) toluene, separated and the water layer was then extracted with (2×50 ml) toluene. The toluene layers were combined and concentrated in vacuo. The residue was purified by silica gel chromatography, eluting with 5% MeOH/CH₂Cl₂ to give 0.59 g (32%) of the title compound.

¹H NMR(CDCl₃) 8.32(1H, s, H-8), 7.91(1H, s, H-2), 5.77(2H, s, NH₂), 5.63(4H, m, CH₂OP), 4.37(2H, t, J=5.0, H-1'), 3.92 (2H,t,J=5.0,H-2'), 3.82 (2H, d, J=7.7, H-4'), 1.18(18H, s, CH₃). ¹³C NMR (CDCl₃) 177.55(C=0), 156.23 (C-6), 153.45(C-2), 150.48(C-4), 142.05(C-8), 119.85(C-5), 82.04 (CH₂OP,d,J=6.0), 71.70(C-2', d, J=9.8), 65.86(C-4', d, J=167), 43.63(C-1') 38.95(CC(=O), 27.11 (CH₃). IR(KBr) 3366, 3178, 2976, 1754, 1660, 1600. MS(Isobutane/DCI) 502 (M+H, 100); Anal. Calcd. for $C_{20}H_{32}N_5O_8P_1$: C, 47.90; H, 6.43; N, 13.96; Found: C, 48.02; H, 6.27; N, 13.63.

Example 10
Synthesis of PMEA, (mono isopropyl, mono pivaloyloxymethyl) ester

To a rapidly stirred solution of 200 mg (0.6 mmol) of monoisopropyl PMEA (example 11) in 5 ml of anhydrous DMF was added 0.83 ml (6.0 mmol) of Et₃N and 0.45 g (3.0 mmol) of chloromethylpivalate. The heterogeneous mixture became homogeneous after addition of Et₃N and was then allowed to stir at 22° C. for about 3 days. The mixture was concentrated in vacuo and the residue was purified by silica gel chromatography, eluting with 10% MeOH/CH₂Cl₂ to give 190 mg (74%) of the title compound.

¹H NMR(CDCl₃) 8.30(1H, s, H-8), 7.91(1H, s, H-2), 5.94(2H, s, NH₂), 5.57(2H, d, J=12.5, CH₂OP), 4.73 (1H, septet, J=6.2, CH), 4.36(2H, t, J=5.0, H-1'), 3.90(2H, t, J=5.0, H-2'), 3.75(2H, d, J=8.0, H-4', 1.25(6H, d, J=6.2, CH₃), 1.17(9H, s, CH₃). ¹³C NMR (CDCl₃) 177(C=0), 155.51(C-6), 152.91(C-2), 149.8 (C-4), 141.43(C-8), 119.36 (C-5), 81.90(CH₂OP, d, J=5.6), 72.18(CHOP, d, J=7.0), 71.19(C-2', d, J=10.0), 65.78 (C-4', d, J=167), 43.37 (C-1'), 38.68((CH₃)₃C), 26.84((CH₃)₃C), 23.92(CH₃CH, d, J=7), 23.85(CH₃CH, d, J=7). IR(KBr) 3432, 1754, 1668, 1602. MS(FAB) 430(M+H, 100); Anal. Calcd. for $C_{17}H_{28}N_5O_6P_1 \cdot 0.50\ H_2O$: C, 46.56; H, 6.66; N, 15.98. Found: C, 46.50; H, 6.61; N, 15.81.

Example 11
Synthesis of PMEA, monocholine ester

A suspension of 2.00 g (7.33 mmol) of PMEA in 30 ml of thionyl chloride was refluxed for about 1 hour. The homogeneous, orange-red solution was cooled and the solvents were removed in vacuo to afford crude dichlorophosphonate. The dichloride was taken up in 40 ml of acetonitrile and then treated with 2.00 g (32.34 mmol) of anhydrous ethylene glycol at reflux for about 16 hours. After cooling to 22° C., the solvents were removed in vacuo. The residue was purified by silica gel chromatography, eluting with MeOH/CH₂Cl₂/NH₄OH 30/70/1 to give 1.42 g (65%) of mono (chloroethyl)ester.

A suspension of 460 mg (1.37 mmol) of the above compound in 30 ml of MeOH was saturated with Me₃N gas at 0° C. The reaction mixture was then sealed in a metal bomb and heated at 65° C. for about 2 days.

After cooling the reaction to 22° C., the solvents were removed in vacuo and the residue was purified by C-18 chromatography, eluting with 15% MeOH/H₂O to give 270 mg (35% from PMEA) of the title compound.

¹H NMR(CD₃OD) 8.24(1H, s, H-8), 8.20(1H, s, H-2), 4.42(2H, t, J=5.0, H-1'), 4.12(2H, CH₂CH₂OP), 3.89(2H, t, J=5.0, H-2'), 3.64(2H,d,J=9.0, H-4'), 3.47 (2H, m, CH₂OP), 3.14(9H, s, CH₃). ¹³C NMR (CD₃OD) 157.55(C-6), 154.03 (C-2), 151.02(C-4), 144.02(C-8), 120.15(C-5), 72.04(C-2'), 68.24(C-4',d, J=159), 68.05 (CH₂OP), 60.10(CH₂CH₂OP,d, J=4.9), 55.02(CH₃), 54.98(CH₃), 54.92(CH₃), 44.95(C-1'). IR(KBr) 3396, 1648, 1602, 1480. MS(FAB) 359(M+H,30); Anal. Calcd. for $C_{13}H_{23}N_6O_4P_1 \cdot 2.5H_2O$: C, 38.60; H, 7.00; N, 20.78; Found: C, 38.26; H, 6.60; N, 20.47.

Example 12
Synthesis of PMEA, di-(propionyloxymethyl ester)

To a rapidly stirred solution of 1.00 g (3.66 mmol) of PMEA in 15 ml of anhydrous DMF was added 2.08 g (7.32 mmol) of N,N'-dicyclohexyl-4-morpholine carboxamidine and 2.23 g (18.3-mmol) of chloromethylpropionate. The heterogeneous mixture became homogeneous within 30 minutes and was then allowed to stir at 22° C. for about 5 days. The insolubles were filtered off and the filtrate was concentrated in vacuo. The residue was purified twice by silica gel chromotography (200:1), eluting with 5%MeOH/$CH_2Cl_2$ to give 0.14 g (9%) of the title compound.

$^1$H NMR($CDCl_3$) 8.29(1H, s, H-8), 7.88(1H, s, H-2), 5.65(2H, s, $NH_2$), 5.60(4H, m, $CH_2OP$), 4.35(2H, t, J=5.0, H1'), 3.89(2H, t, J=5.0, H-2') 3.80(2H, d, J=7.8, H-4'), 2.34(4H, q, J=7.5, $CH_3CH_2$) 1.10 (6H, t, J=7.5, $CH_3$). IR(KBr) 3290, 3122, 1766, 1666, 1602. MS(FAB) 446(M+ H, 100); Anal. Calcd. for $C_{16}H_{24}N_5O_8P_1$: C, 43.15; H, 5.43; N, 15.72; Found: C, 43.07; H, 5.46; N, 15.42.

Example 13
Synthesis of PMEA, di-(isobutyrloxymethyl ester)

To a rapidly stirred solution of 1.00 g (3.66 mmol) of PMEA in 15 ml of anhydrous DMF was added 2.08 g (7.32 mmol) of N,N'-dicyclohexyl-4-morpholine carboxamidine and 2.48 g (18.3 mmol) of chloromethlyisobutyrate. The heterogeneous mixture became homogeneous within 30 minutes and was then allowed to stir at 22° C. for 5 days. The mixture was concentrated in vacuo, partitioned between (50 ml) water and (50 ml)toluene. The aqueous layer was extracted with (250 ml) toluene and the combined organic layer was concentrated in vacuo. The residue was purified by silica gel chromatography, eluting with 5% MeOH/$CH_2Cl_2$ to give 0.16 g (9%) of the title compound.

$^1$H NMR($CDCl_3$) 8.31(1H, s, H-8), 8.28(1H, s, H-2), 5.68(2H, s, $NH_2$), 5.59(4H, m, $CH_2OP$), 4.33(2H, t, J=5.0, H-1'), 3.88(2H, t, J=5.0, H-2'), 3.78(2H, d, J=7.7H, H-4'), 2.52(2H, apparent heptet, J=7.0, CH), 1.11(6H, d, J=7.0, $CH_3$). IR(KBr) 3360, 2980, 1758, 1660, 1602; MS(Isobutane/DCI) 474(M+H, 100); Anal. Calcd. for $C_{18}H_{28}N_5O_8P_1$, 0.65 $H_2O$: C, 44.56; H, 6.09; N, 14.44; Found: C, 45.67; H, 5.96; N, 14.79.

Example 14
Synthesis of PMEA, (mono ethyl, mono isobutyryloxymethyl) ester

To a rapidly stirred solution of 400 mg (1.33 mmol) of monoethyl PMEA in 15 ml of anhydrous DMF was added 2.00 ml (14.3 mmol) of $Et_3N$ and 1.0 g (6.7 mmol) of chloromethylpivalate. The heterogeneous mixture became homogeneous after addition of $Et_3N$ and was then allowed to stir at 22° C. for 2 days. The mixture was concentrated in vacuo and the residue was purified by silica gel chromatography, eluting with 10% MeOH/$CH_2Cl_2$ to give 180 mg (33%) of the title compound.

$^1$H NMR($CDCl_3$) 8.32(1H, s, H-8), 7.92(1H, s, H-2), 5.74(2H, s, $NH_2$), 5.62(2H, m, $OCH_2OP$), 4.38 (2H, t, J=5.0, H-1'), 4.10(2H, m, $CH_3CH_2OP$), 3.92(2H, t, J=5.0, H-2'), 3.79(2H, d, J=8.0, H-4'), 1.27 (3H, t, J=7.0, $CH_3CH_2$), 1.18 (9H, s, (($CH_3$)C). $^{13}$C NMR ($CDCl_3$) 176.87(C=O), 155.40 (C-6), 152.94(C-2), 149.8(C-4), 141.51(C-8), 119.7(C-5), 81.85($CH_2OP$, d, J=6.2), 71.26(C-2', d, J=10.2), 65.46(C-4', d, J=167), 62.73($CH_2CH_3$, d, J=7.0), 43.49(C-1'), 38.70( ($CH_3)_3C$), 26.84(($CH_3)_3C$), 16.27($CH_2CH_3$, d, J=5.8), IR(KBr) 3288, 3120, 2982, 1752, 1666, 1600. MS(FAB) 416(M+H, 100); Anal. Calcd. for $C_{16}H_{26}N_5O_6P_1$, 0.5$H_2O$: C, 45.28; H, 6.41; N, 16.51; Found: C, 45.47; H, 6.34; N, 16.55.

Example 15
Synthesis of PMEA, mono pivaloyloxymethyl ester

To a solution of sodium hydride(0.95 g, 80%, 31.7 mmol) and benzylalcohol (6.8 ml, 63.5 mmol) in anhydrous DMSO (50 ml) was added with stirring a solution of PMEA, diphenyl ester (3.4 g, 8 mmol, example 26) in DMSO(50 ml). The mixture was allowed to stir at 22° C. for 1 h and concentrated to a volume of approximately 25 ml. EtOAc (200 mL) was added and the precipitate was collected by vacuum filtration. The precipitate was purified by C-18 chromatagrophy, eluting with 20% MeOH/$H_2O$ to give 2.09 g 68%) of PMEA, monobenzylester, sodium salt.

To 600 mg (1.56 mmoles) of the above compound in 14 ml of anhydrous DMF was added 2.16 ml (15.5 mmoles) of $Et_3N$ and 1.44 g (9.61 mmol) of chloromethylpivalate. The mixture was allowed to stir at 22° C. for 2 days, concentrated in vacuo and the resulting residue was used crude in the following step.

To a stirred solution of the crude mixed ester (300 mg) in 17 ml of EtOH and 17 ml of $H_2O$ was added 3.45 ml of cyclohexene and 0.225 g of 20% Pd(OH)$_2$/C. The mixture was heated at reflux for 1 h, concentrated in vacuo and the residue purified by C-18 chromatography, eluting with 100% $H_2O$ to give 270 mg (31% from PMEA, diphenyl ester) of the title compound.

$^1$H NMR($d_6$-DMSO) 8.09(2H, s, H-8, H-2), 7.17(2H, s, $NH_2$), 5.44(2H, m, $CH_2OP$), 4.26(2H, t, J=5.0, H1'), 3.83 (2H,t, J=5.0, H-2), 3.47(2H, d, J=8.0, H-4), 1.04(9H, S, $CH_3$). $^{13}$C NMR ($d_6$-DMSO) 176.70(C=0), 155.98(C-6), 152.39(C-2), 149.55(C-4), 141.30(C-8), 118.59(C-5), 83.14 ($CH_2OP$), 69.89(C-2'), 64.5(C-4'), 42.84 (C1'), 38.13 (($CH_3)_3$ C) 26.69($CH_3$). IR(KBr) 3360, 1742, 1648, 1602; MS(FAB) 386(M-H, 100). HRMS: Calculated: 388.1386; Found: 388.1377;

Example 16
Synthesis of PMEA, (mono isopropyl, monophenyl) ester

A suspension of 0.75 g (2.1 mmol) of monophenyl PMEA in 20 ml of thionyl chloride was refluxed for 1 h. The homogeneous, orange-red solution was cooled and the solvents were removed in vacuo to afford crude monochlorophosphonate. The residue was taken up in 40 ml of isopropyl alcohol and stirred for 16 h at 22° C. The solvents were removed in vacuo and the residue was purified by silica gel chromatography, eluting with 10% MeOH/$CH_2Cl_2$ to give 0.24 g (29%) of the title compound.

Mp 96°–99° C. $^1$H NMR($CDCl_3$) 8.31(1H, s, H-8), 7.87 (1H, s, H-2), 7.19(5H, m, Ph), 5.96(2H, s, $NH_2$), 4.80 (1H, apparent heptet, J=6.2, CH), 4.36(2H, t, J=5.0, H-1'), 3.93 (2H, t, J=5.0, H-2'), 3.86(2H, d, J=7.9, H-4'), 1.26(3H, d, J=6.2, $CH_3$), 1.21(3H, d, J=6.2 $CH_3$). $^{13}$C NMR ($CDCl_3$) 155.52(C-6), 152.88(C-2), 150.13(ArC, d, J=8.3), 149.89 (C-4), 141.46(C-8), 129.71(ArC), 125.14(ArC), 120.50 (ArC, d, J=4.5), 119.43(C-5), 72.65(CH, d, J=7.3), 71.18(C-2, d, J=10.6), 65.27(C-4', d, J=167.5), 43.45(C-1'), 23.93 ($CH_3$, d, J=4.5), 23.82($CH_3$, d, J=4.5). IR(KBr) 3290, 3116, 1670, 1600; MS(Isobutane/DCI) 392(M+H, 100); Anal. Calcd. for $C_{17}H_{22}N_5O_4P_1$: C,52.17; H, 5.66; N, 17.89; Found: C, 52.01; H, 5.57; N, 17.64.

Example 17
Synthesis of PMEA, (mono-N,N-diethylacetamide, mono pivaloyloxymethyl) ester To a suspension of 0.100 g (0.239 mmol) of PMEA, mono-N,N-diethylacetamide ester (sodium salt) (Example 27) in 2.5 mL of $CH_3CN$ was added 0.25 mL of $Et_3N$, whereupon the reaction became homogeneous. To this mixture was added 0.17 mL (1.19 mmol) of chloromethyl pivalate. The reaction was stirred at 22° C. for 24 h, evaporated to dryness in vacuo, and purified on a 20 mm flash column. The title compound eluted with 10% MeOH/ $CH_2Cl_2$ to give 25 mg (21%) of a colorless oil.

$^1$H NMR (CDCl$_3$) 8.25 (1H, s, H-8), 7.94 (1H, s, H-2), 6.26 (2H, s, NH$_2$), 5.65 (1H, dd, J=12.3, 5.4, OCH$_2$O), 5.60 (1H, dd, J=12.3, 4.8, OCH$_2$O), 4.75 (1H, dd, J=14.7, 10.8, OCH$_2$C(O)), 4.56 (1H, dd, J=14.5, 14.3, OCH$_2$C(O)), 4.32 (2H, dd, J=5.7, 4.4, H-1'), 3.97 (2H, d, J=8.4, H-4$^{1'}$), 3.91 (2H, t, J=4.8, H-2'), 3.28 (2H, q, J=7.5, CH$_2$CH$_3$), 3.09 (1H, q, J=7.2, CH$_2$CH$_3$), 1.12 (9H, s, (CH$_3$)$_3$), 1.07 (3H, m, CH$_3$CH$_2$), 1.05, (3H, t, J=6.9, CH$_3$CH$_2$). $^{13}$C NMR (CDCl$_3$) 177.85 (C(O)O), 166.25 (C(O)N), 156.34 (C-6), 153.48 (C-2), 150.49 (C-4), 14 2.22 (C-8), 119.79 (C-5), 81.94 ((CH$_3$)$_3$C),81.71 (OCH$_2$O), 71.55 (C-21, d, J=10), 65.10 (C-4', d, J=165), 63.99 (CCH$_2$OP), 43.53 (C-11), 41.03 (NCH$_2$), 40.78 (NCH$_2$), 27.00 ((CH$_3$)$_3$), 14.21 (CH$_3$CH$_2$), 13.00 (CH$_3$CH$_2$). MS (FAB) 501 (M+H, 100). IR 3500–3000, 2978, 1750, 1654, 1600, 1480, 1250; Anal. Calcd for: $C_{20}H_{33}N_6O_7P.0.5$ H$_2$O; C, 47.15; H, 6.72; N, 16.50; Found: C, 47.30; H, 6.58; N, 16.14.

The following examples were prepared by the methods given in Table I.

Example 18
PMEA, cyclic propanyldiester

Mp 195°–199° C. $^1$H NMR (d$_6$-DMSO) 8.13 (1H, s, H-8), 8.12 (1H, s, H-2), 4.35 (2H, t, J=4.8, H-1'), 4.2 (4H, m, CH$_2$OP), 3.95 (2H, d, J=8.8, H-4'), 3.86 (2H, t, J=4.8, H-2'), 1.98 (1H, m, CH$_2$CH$_2$CH$_2$), 1.55 (1H, m, CH$_2$C-H$_2$CH$_2$). $^{13}$C NMR (d$_6$-DMSO) 156.01 (C-6), 152.48 (C-2), 149.69 (C-4), 141.11 (C-8), 118.68 (C-5), 70.71 (C-2', d, J=13.8), 68.30 (CH$_2$OP, d, J=6.9), 64.55 (C-4', d, J=158), 42.52 (C-1'), 25.85 (CH$_2$CH$_2$CH$_2$, d, J=9.0). IR (KBr) 3351,3169, 1660, 1601, 1256, 1063. MS (FAB) 314 (M+H, 100); Anal. Calcd for: $C_{11}H_{16}N_5O_4P.1.5$ H$_2$O; C, 38.85; H, 5.63; N, 20.60; Found: C, 38.63; H, 5.46; N, 20.49.

Example 19
PMEA bis-diethylamide

Mp 93°–96°C. $^1$H NMR (d$_6$-DMSO) 8.11 (H, s, H-8), 8.07 (1H, s, H-2), 7.18 (2H, s, NH$_2$), 4.31 (2H, t, J=4.8, H-1'), 3.85 (2H, t, J=4.8, H-2'), 3.68 (2H, d, J=8.1, H-4'), 2.70 (8H, (m, CH$_3$CH$_2$), 0.86 (12H, t, J=7.0, CH$_3$). $^{13}$C NMR (d$_6$-DMSO) 155.98 (C-6), 152.33 (C-2), 149.63 (C-4), 141.04 (C-8), 118.75 (C-5), 70.30 (C-2', d, J=13.0), 66.30 (C-4'), d, J=133), 42.63 (C-1'), 37.53 (CH$_3$CH$_2$), d, J=4.1), 13.93 (CH$_3$, d, J=1.9). IR (KBr) 3370–2935, 2875, 1680, 1649, 1605, 1211. MS (FAB) 384 (M+H), 100); Anal. Calcd for: $C_{16}H_{30}N_7O_2P.0.5$ H$_2$O; C, 48.96; H, 7.96; N, 24.99; Found: C, 48.85; H, 7.77; N, 24.92.

Example 20
PMEA, isopropyl ester (sodium salt)

Mp 77°–850° C. turned to glass and melted over next 40° C. $^1$H NMR (d$_6$-DMSO) 8.19 (H, s, H-8), 8.13 (1H, s, H-2), 7.22 (2H, s, NH$_2$), 4.30 (2H, t, J=4.4, H-1'), 4.10 (1H, m, OCH), 3.76 (2H, t, J=4.4, H-2'), 3.31 (2H, d, J=8.6, H-4'), 0.90 (6H, d, J=6.0, CH$_3$). $^{13}$C (d$_6$-DMSO; 90 MHz), 155.90 (C-6), 152.35 (C-2), 149.54 (C-4), 141.39 (C-8), 118.53 (C-5), 70.23 (OCH, d, J=10), 68.70 (C-4', d, J=192), 65.55 (C-2', d, J=5), 42.72 (C-1'), 24.43 (CH$_3$). IR (Film) 3321, 3163, 1647, 1601, 1578. MS (FAB) 338 (M+H, 70); Anal. Calcd for: $C_{11}H_{17}N_5O_4P_1Na_1.H_2O$; C, 37.18; H, 5.38; N, 19.71; Found: C, 37.11; H, 5.49; N, 19.71.

Example 21
PMEA, cyclic (2,2-dimethyl)propanyl diester

Mp 224°–226° C. $^1$H NMR (d$_6$-DMSO) 8.11 (2H, s, H-8, H-2), 7.21 (2H, s, NH$_2$), 4.34 (2H, t, J=5.0, H-1'), 3.99 (2H, d, J=8.7, H-4'), 3.91 (2H, t, J=5.0, H-2'), 3.95–3.75 (4H, m, CH$_2$C(CH$_3$)$_2$CH$_2$), 1.06 (3H, s, CH$_3$), 0.67 (3H, s, CH$_3$). $^{13}$C NMR (d$_6$-DMSO; 50 MHz) 155.89 (C-6), 152.33 (C-2), 149.53 (C-4), 140.86 (C-8), 118.57 (C-5), 76.67 (CH$_2$C (CH$_3$)$_2$CH$_2$, d, J=6.8), 70.44 (C-2', d, J=13.7), 64.43 (C-4', d J=157), 42.43 (C-1'), 31.70 (C(CH$_3$)$_2$, d, J=7.6), 21.05 (CH$_3$), 19.46 (CH$_3$). IR (KBr) 3417, 3324, 3152, 2970, 1668, 1650, 1602. MS (FAB) 342 (M+H, 100); Anal. Calcd for: $C_{13}H_{20}N_5O_4P.0.25$ H$_2$O; C, 45.18; H, 5.97; N, 20.27; Found: C, 45.58; H, 6.05; N, 20.05.

Example 22
PMEA, 3-hydroxypropanyl ester, (sodium salt)

$^1$H NMR (d$_6$-DMSO) 8.17 (1H, s, H-8), 8.11 (1H, s, H-2), 7.20 (2H, s, NH$_2$), 5.11 (1H, t, OH), 4.28 (2H, t, J=4.7, H-1'), 3.76 (2H, t, J=4.7, H-2'), 3.64 (2H, q, J=6.6, CH$_2$CH$_2$OP), 3.41 (2H, d, J=8.0, H-4'), 3.35 (2H, t, J=6.2, HOCH$_2$), 1.45 (2H, m, HOCH$_2$CH$_2$). $^{13}$C NMR (d$_6$-DMSO; 50 MHz) 155.82 (C-6), 152.25 (C-2), 149.43 (C-4), 141.38 (C-8), 118.43 (C-5), 69.77 (C-2', d, J=10), 67.42 (C-4', d, J=152), 59.33 (CH$_2$CH$_2$OP, d, J=6), 56.88 (HOCH$_2$), 42.60 (C1'), 33.91 (HOCH$_2$CH$_2$; d, J=4). IR (KBr) 3412, 2956, 1647, 1604, 1482, 1421. MS (FAB) 354 (M+H, 17); Anal. Calcd for: $C_{11}H_{17}N_5O_5P_1Na_1.2.5$ H$_2$O; C, 33.17; H, 5.56; N, 17.59; Found: C, 33.32, H, 5.28; N, 17.63.

Example 23
PMEA, monooctyl ester $^1$H NMR (d$_5$-pyridine) 9.47, 9.34 (2H, 2s, H-2, H-8), 5.46 (2H, t, J=4.5), 5.3–5.1 (6H, m, H-2', H-4', CH$_2$CH$_2$CH$_2$O), 2.68 (2H, m, CH$_2$CH$_2$CH$_2$O), 2.33 (2H, m, CH$_2$CH$_2$CH$_2$O), 2.1 (8H, m, CH$_3$(CH$_2$)$_4$)), 1.79 (3H, t, J=6.5, CH$_3$). IR (KBr) 3416, 2928, 1690, 1065. MS (FAB) 386 (M+H, 100); Anal. Calcd for: $C_{16}H_{28}N_5O_4P.H_2$ O.Na.0.6 NaCl; C, 41.59; H, 6.54; N, 15.15; Found: C, 41.80; H, 6.87; N, 15.02.

Example 24
PMEA, dimethyl-ester

Mp 133°–135° C. $^1$H NMR (d$_6$-DMSO) 8.14 (1H, s, H-8), 8.10 (1H, s, H-2), 7.29 (2, s, NH$_2$), 4.33 (2H, t, J=5.0, H-1') 3.90 (2H, d, J=8.3, H-4'), 3.85 (2H, t, J=5.0, H-2'), 3.57 (6H, d, J=10.6, CH$_3$). $^{13}$C NMR (d$_6$-DMSO) 155.87 (C-6), 152.87 (C-2), 149.59 (C-4), 141.27 (C-8), 118.65 (C-5), 70.40 (C-2', d, J=11.5), 63.17 (C-4', d, J=182), 52.79 (CH$_3$, d, J=6.4), 42.48 (C-1'). IR (KBr) 3400, 3188, 1671, 1647, 1605. MS (methane/DCI) 302 (M+H, 100); Anal. Calcd for: $C_{10}H_{16}N_5O_4P.0.6$ H$_2$O; C, 38.43; H, 5.56; N, 22.41; Found: C, 38.76; H, 5.45; N, 22.18.

Example 25
PMEA, monomethyl ester, (sodium salt)

$^1$H NMR (d$_6$-DMSO) 8.19 (1H, s, H-8), 8.11 (1H, s, H-2), 7.17 (2H, s, NH$_2$), 4.27 (2H, t, J=5.0, H-1'), 3.77 (2H, t, J=5.0, H-2'), 3.35 (2H, d, J=8.0, H-4'), 3.24 (3H, d, J=10.0, CH$_3$). $^{13}$C (d$_6$-DMSO; 90 MHz) 155.87 (C-6), 152.26 (C-2), 149.49 (C-4), 141.44 (C-8), 118.51 (C-5), 69.69 (C-2', d, J=9), 67.09 (C-4', d, J=152), 50.78 (CH$_3$, d, J=5), 42.64 (C-1'). IR (KBr) 3421, 3195, 1649, 1605, 1578, 1516. MS (FAB) 310 (M+H, 23); Anal. Calcd for $C_9H_{13}N_5O_4P_1Na_1.3H_2O.NaCl$; C, 25.63; H, 4.54; N, 16.61; Found: C, 25.39; H, 4.84; N, 16.73; HRMS Calcd 310.0681; Found: 310.0688

Example 26
PMEA, mono- 3-amino - 2,2-dimethylpropyl amide $^1$H NMR (D$_2$O)-8.13 (1H, s, H-8), 8.11 (1H, s, H-2), 4.36 (2H, t, J=5, H-1'), 3.90 (2H, t, J=5, H-2'), 3.53 (2H, d, J=8.5, H-4'), 2.71 (2H, s, NH$_2$CH$_2$), 2.07 (2H, d, J=9.4, CH$_2$NH), 0.70 (6H, s, CH$_3$). $^{13}$C NMR (D$_2$O) 157.25 (C-6), 154.19 (C-2), 150.78 (C-4), 144.73 (C-8), 120.03 (C-5), 72.24 (C-2', d, J=12.5), 69.63 (C-4', d, J=143), 50.05 (CH$_2$NH), 48.41 (H$_2$NCH$_2$), 45.53 (C-1'), 35.36 (C(CH$_3$)$_2$, d, J=4), 24.09 (CH$_3$). IR (KBr) 3786, 3381, 1648, 1605, 1478. MS (FAB) 380 (M+H, 20). HR-MS (M+H); Anal. Calcd for C$_{13}$H$_{23}$N$_7$O$_3$P$_1$Na$_1$: 380.1576; Found: 380.1567.

Example 27
PMEA, mono-hydroxy-2,2-dimethylpropyl ester $^1$H NMR (d$_6$-DMSO) 8.14 (1H, s, H-8), 8.09 (1H, s, H-2), 7.16 (2H, s, NH$_2$), 5.84 (1H, t, OH), 4.27 (2H, t, J=4.9, H-1'), 3.77 (2H, t, J=4.9, H-2'), 3.33 (2H, d, J=8.7, H-4'), 3.24 (2H, d, J=10, C(CH$_3$)$_2$CH$_2$OP), 3.00 (2H, d, HOCH$_2$), 0.63 (6H, s, CH$_3$). $^{13}$C NMR (d$_6$-DMSO, 50 MHz), 155.84 (C-6), 152.21 (C-2), 149.45 (C-4), 141.26 (C-8), 118.48 (C-5), 69.71 (C-2', d, J=9.2), 68.27 (C(CH$_3$)$_2$CH$_2$OP, d, J=6.2), 67.48 (C-4', d, J=152), 65.93 (HOCH$_2$), 42.57 (C1'), 36.71 (C(CH$_3$)$_2$, d, J=2.5), 21.35 (CH$_3$). IR (KBr) 3426, 2960, 2883, 1645, 1478, 1417. MS (FAB) 360 (M+H, 100); Anal. Calcd. for C$_{13}$H$_{22}$N$_5$O$_5$P.1.3 H$_2$O: C, 40.77; H, 6.48; N, 18.29; Found: C, 40.96; H, 6.16; N, 17.95

Example 28
PMEA, cyclic-2,2-dimethyl-propanyl diamide $^1$H NMR (d$_6$-DMSO) 8.11 (1H, s, H-8), 8.10 (1H, s, H-2), 7.18 (2H, s, NH$_2$), 4.30 (2H, t, J=5.0, H-1'), 3.83 (2H, t, J=5.0, H-2'), 3.63 (2H, d, J=7.5, H-4'), 4.27 (2H, s, NH, NH), 2.65–2.40 (4H, m, CH$_2$C(CH$_3$)$_2$CH$_2$), 0.98 (3H, s, CH$_3$), 0.64 (3H, s, CH$_3$). $^{13}$C NMR (d$_6$-DMSO) 156.01 (C-6), 152.42 (C-2), 149.60 (C-4), 141.24 (C-8), 118.68 (C-5), 70.35 (C-2', d, J=11.2), 68.53 (C-4', d, J=131), 52.72 (CH$_2$C(CH$_3$)$_2$CH$_2$, d, J=2.3), 42.78 (C-1'), 30.54 (C(CH$_3$)$_2$, d, J=5.6), 24.82 (CH$_3$), 23.25 (CH$_3$). IR (KBr) 3100, 2980, 2940, 1650, 1605. MS (FAB) 340 (M+H, 100). HR-MS (M+H); Anal. Calcd for C$_{13}$H$_{22}$N$_7$O$_2$P: 340.1651. Found: 340.1647.

Example 29
PMEA, N,N'-dimethyl-cyclic propanyl diamide $^1$H NMR (d$_6$-DMSO) 8.08 (2H, s, H-8, H-2), 7.14 (2H, s, NH$_2$), 4.28 (2H, br s, H-1'), 3.80 (2H, br s, H-2'), 3.73 (2H, dd, J=7.6, 2.8 H-4'), 2.85–2.60 (4H, m, CH$_3$NCH$_2$), 1.8–1.3 (2H, m, CH$_2$CH$_2$CH$_2$), 2.36 (3H, d, J=3, NCH$_3$), 2.33 (3H, d, J=3, NCH$_3$). $^{13}$C NMR (d$_6$-DMSO) 156.02 (C-6), 152.44 (C-2), 149.77 (C-4), 141.09 (C-8), 118.74 (C-5), 70.44 (C-2', d, J=14), 65.42 (C-4', d, J=164), 50.22 (NCH$_3$), 42.85 (C-1'), 34.28 (CH$_3$NCH$_2$), 24.79 (CH$_2$CH$_2$CH$_2$). IR (KBr) 3300, 3180, 2930, 2877, 1651, 1600. MS (methane/DCI) 340 (M+H, 100); Anal. Calcd for C$_{13}$H$_{22}$N$_7$O$_2$P.0.9 HCl: C, 41.93; H, 6.22; N, 26.33; Found: C, 42.33; H, 6.19; N, 25.93; HR-MS (M+H) Calcd for C$_{13}$H$_{22}$N$_7$O$_2$P: 340.1651. Found: 340.1649.

Example 30
PMEA, mono-N,N,-diethylacetamide ester

Mp 189°–191° C. $^1$H NMR (d$_6$-DMSO) 8.16 (1H, s, H-8), 8.14 (1H, s, H-2), 7.55 (2H, s, NH$_2$), 4.80 (2H, d, J=9.0, C(O)CH$_2$O), 4.31 (2H, t, J=5.0, H-1'), 4.03 (2H, t, J=5.0, H-2'), 3.74 (2H, d, J=8.5, H-4'), 3.22 (2H, q, J=7, CH$_3$CH$_2$), 3.16 (2H, q, J=7, CH$_3$CH$_2$), 1.01 (3H, t, J=7, CH$_3$), 1.01 (3H, t, J=7, CH$_3$). $^{13}$C NMR (CF$_3$CO$_2$D; 90 MHz) 166.10 (C=O), 150.04, 148.67 (C-6, C-4), 144.74, 144.55 (C-2, C-8), 117.96 (C-5), 70.05 (C-2', d, J=10), 65.37 (C-4', d, J=162), 62.87 (C(O)CH$_2$, d, J=5), 43.44 (C-1'), 14.06 (CH$_3$), 12.91 (CH$_3$). IR (KBr) 3392, 3093, 1692, 1650, 1515. MS (methane/DCI) 500 (M+H, 30), 132 (100). HR-MS (M+H); Anal. Calcd for C$_{14}$H$_{23}$N$_6$O$_5$P: 387.1546; Found: 387.1543.

Example 31
PMEA, mono-acetic acid ester

Mp 197°–200° C. $^1$H NMR (d$_6$-DMSO) 8.19 (1H, s, H-8), 8.17 (1H, s, H-2), 7.75 (2H, S, NH$_2$), 4.34 (2H, d, J=4, C(O)CH$_2$O), 4.32 (2H, t, J=5, H-1'), 3.86 (2H, t, J=5, H-2'), 3.71 (2H, d, J=8, H-4'). $^{13}$C NMR (d$_6$-DMSO) 177.19 (C=0, d, J=7), 156.84 (C-6), 153.72 (C-2), 150.03 (C-4), 144.05 (C-8), 119.44 (C-5), 71.66 (C-2', d, J=11), 67.39 (C-4', d, J=157), 64.90 (C(O)CH$_2$O, d, J=6), 44.59 (C-1'). IR (KBr) 3366, 3109, 1690, 1611, 1516, 1415. MS (FAB) 332 (M+H, 55); Anal. Calcd for C$_{10}$H$_{14}$N$_5$O$_6$P.0.3 H$_2$O: C, 35.74; H, 4.38; N, 20.85; Found: C, 35.41; H, 4.43; N, 20.60.

Example 32
PMEA, di(butylacetate ester)

Mp 78°–80° C. $^1$H NMR (d$_6$-DMSO) 8.11 (1H, s, H-8), 8.06 (1H, s, H-2), 7.18 (2H, s, NH$_2$), 4.62 (4H, d, J=11, C(O)CH$_2$OP), 4.31 (2H, t, J=5.0, H-1'), 4.07 (4H, t, J=7, CH$_2$OC(O)), 4.00 (2H, d, J=8, H-4'), 3.90 (2H, t, J=5, H-2'), 1.54 (4H, apparent quintet, J=7, CH$_3$CH$_2$CH$_2$), 1.31 (4H, apparent hextet, J=7.7, CH$_3$CH$_2$), 0.86 (6H, t, J=7, CH$_3$). $^{13}$C NMR (d$_6$-DMSO) 168.16 (C=0, d, J=4.7), 156.03 (C-6), 152.44 (C-2), 149.59 (C-4), 141.10 (C-8), 118.65 (C-5), 70.58 (C-2', d, J=10), 64.70 (CH$_2$OC(O)), 64.19 (C-4', d, J=165), 62.05 (CH$_2$O, d, J=6), 42.45 (C1'), 30.10 (CH$_3$CH$_2$CH$_2$), 18.53 (CH$_3$CH$_2$), 13.56 (CH$_3$). IR (KBr) 3339, 3158, 2994, 2962, 1764, 1662, 1600. MS (methane/DCI) 502 (M+H, 100); Anal. Calcd for C$_{20}$H$_{32}$N$_5$O$_8$P: C, 47.90; H, 6.43; N, 13.97; Found: C, 47.94; H, 6.40; N, 13.90.

Example 33
PMEA, di(ethylacetate ester)

Mp 82°–84° C. $^1$H NMR (d$_6$-DMSO) 8.11 (1H, s, H-8), 8.06 (1H, s, H-2), 7.16 (2H, s, NH$_2$), 4.59 (4H, d, J=11, C(O)CH$_2$O), 4.30 (2H, t, J=5.0, H-1'), 4.13 (4H, q, J=7.0, CH$_3$CH$_2$), 4.00 (2H, d, J=8.0, H-4'), 3.98 (2H, t, J=5.0, H-2'), 1.18 (6H, t, J=7.0, CH$_3$). $^{13}$C NMR (D$_2$O) 171.44 (C=O, d, J=5), 156.90 (C-6), 153.85 (C-2), 150.56 (C-4), 144.66 (C-8), 119.86 (C-5), 73.02 (C-2', d, J=10.5), 66.12 (C-4', d, J=166), 64.85 (CH$_3$CH$_2$), 64.75 (C(O)CH$_2$O), 45.57 (C1'), 15.22 (CH$_3$). IR (KBr) 3296, 3122, 1764, 1667, 1602. MS (methane/DCI) 446 (M+H, 100); Anal. Calcd for C$_{16}$H$_{24}$N$_5$O$_8$P: C, 43.15; H, 5.43; N, 15.72; Found: C, 43.04; H, 5.33; N, 15.58.

Example 34
PMEA, monohentyl ester (sodium salt)

Mp 223°–228° C. $^1$H NMR (d$_6$-DMSO) 8.14 (1H, s, H-8), 8.13 (1H, s, H-2), 7.50 (2H, s, NH$_2$), 7.25 (2H, t, J=8, ArH), 7.07 (1H, t, J=8, ArH), 7.01 (2H, d, J=8, ArH), 4.33 (2H, t, J=5, H-1'), 3.89 (2H, t, J=5, H-2'), 3.73 (2H, d, J=8, H-4'). $^{13}$C NMR (D20; Partial spectrum) 131.46, 126.06 (ArC), 122.27 (ArC, d, J=3d5), 72.27 (C-2; d, J=12), 67.68 (C-4', d, J=160), 46.08 (C-1'). IR (KBr) 3389, 3068, 1693, 1594. MS (FAB) 350 (M+H, 40). Anal. Calcd for C$_{14}$H$_{16}$N$_5$O$_4$P.H$_2$O.0.45 Na: C, 44.45; H, 4.81; N, 18.51; Found: C, 44.45; H, 4.45; N, 18.45.

Example 35
PMEA, diphenyl ester

Mp 103°–114° C. $^1$H NMR (d$_6$-DMSO) 8.15 (1H, s, H-8), 8.11 (1H, s, H-2), 7.40 (2H, s, NH$_2$), 7.34 (4H, t, J=7, ArH), 7.20 (2H, t, J=7, ArH), 7.04 (4H, t, J=7, ArH), 4.38 (2H, t, J=5, H-1'), 4.24 (2H, d, J-8, H-4'), 3.98 (2H, t, J=5, H-2'). $^{13}$C NMR (d$_6$-DMSO) 155.51 (C-6), 151.77 (C-2), 149.57 (C-4), 141.46 (C-8), 130.02, 125.49, (ArC), 120.56 (ArC, d, J=4), 118.71 (C-5), 70.58 (C-2', d, J=12), 63.52 (C-4', d, J=164), 42.68 (C-1'). IR (KBr) 3270, 3100, 1675, 1646,

Example 36
PMEA, mono-N,N-diisopropylacetamide ester (sodium salt)

Mp 219°–221° C. $^1$H NMR (d$_6$-DMSO) 8.14 (1H, s, H-8), 8.13 (1H, s, H-2), 7.37 (2H, s, NH$_2$), 4.45 (2H, d, J=9, CH$_2$OP), 4.31 (2H, t, J=5, H-1'), 3.88 (2H, t, J=5, H-2'), 3.74 (2H, d, J=8, H-4'), 3.43 (2H, m, CH(CH$_3$)$_2$), 1.26 (6H, d, J=6, CH$_3$), 1.08 (6H, d, J=6, CH$_3$). $^{13}$C NMR (d$_6$-DMSO/D$_2$O) 170 (C=O), 156.90 (C-6), 153.89 (C-2), 150.35 (C-4), 144.29 (C-8), 119.68 (C-5), 71.89 (C-2', d, J=12), 67.81 (C-4', d, J=158), 65.25 (CH$_2$OP, d, J=5), 49.72 (CH(CH$_3$)$_2$), 47.30 (CH(CH$_3$)$_2$), 45.00 (C-1'), 21.21 (CH$_3$). IR (KBr) 3425, 2969, 1691, 1643, 1515. MS (FAB) 415 (M+H, 100); Anal. Calcd for C$_{16}$H$_{27}$N$_6$O$_5$P.0.67 H$_2$O.0.5 Na: C, 43.87; H, 6.52; N, 19.19; Found: C, 43.92; H, 6.17; N, 18.79.

Example 37
PMEA, di-(p-nitro-benzyl ester)

Mp 190°–193° C. $^1$H NMR (d$_6$-DMSO) 8.16 (4H, d, J=8, ArH), 8.09 (1H, s, H-8), 8.08 (1H, s, H-2), 7.51 (4H, d, J=8, ArH), 7.17 (2H, s, NH$_2$), 5.10 (4H, d, J=8, ArCH$_2$O), 4.32 (2H, t, J=5, H-1'), 4.07 (2H, d, J=8, H-4'), 3.90 (2H, t, J=5, H-2'). $^{13}$C NMR (d$_6$-DMSO) 155.97 (C-6), 152.94 (C-2), 149.62 (C-4), 147.19, 143.96 (ArC), 141.13 (C-8), 128.15, 123.56 (ArC), 118.65 (C-5), 70.62 (C-2', d, J=7), 65.86 (ArCH$_2$O, d, J=6), 63.75 (C-4', d, J=162), 42.49 (C-1'). IR (KBr) 3420, 3268, 3110, 1674, 1642, 1604. MS (FAB) 544 (M+H, 60); Anal. Calcd for C$_{22}$H$_{22}$N$_7$O$_8$P: C, 48.63; H, 4.09; N, 18.05; Found: C, 48.61; H, 4.01; N, 18.04.

Example 38
PMEA, mono-p-nitro-benzyl ester, (sodium salt)

Mp 230°–240° C. $^1$H NMR (d$_6$-DMSO) 8.19 (2H, d, J=8.6, ArH), 8.12 (1H, s, H-8), 8.11 (1H, s, H-2), 7.54 (2H, d, J=8.6, ArH), 4.93 (2H, d, J=7.7, ArCH$_2$O), 4.63 (2H, t, J=5, H-1'), 4.31 (2H, t, J=5, H-2'), 3.72 (2H, d, J=8.6, H-4'). IR (KBr) 3742, 1930, 1692, 1606, 1518. MS (FAB) 409 (M+H, 27); Anal. Calcd for C$_{15}$H$_{17}$N$_6$O$_6$P.0.75 H$_2$O.0.5 Na: C, 41.58; H, 4.30; N, 19.40; Found: C, 41.37; H, 3.92; N, 19.03.

Example 39
PMEA, di-(2,2,2-trichloroethyl ester)

Mp 155°–157° C. $^1$H NMR (d$_6$-DMSO) 8.11 (1H, s, H-8), 8.08 (1H, s, H-2), 7.16 (2H, s, NH$_2$), 4.68 (2H, d, J=7, CCl$_3$CH$_2$), 4.67 (2H, d, J=7, CCl$_3$CH$_2$), 4.34 (2H, t, J=5, H-1'), 4.18 (2H, d, J=8, H-4'), 3.95 (2H, t, J=5, H-2'). $^{13}$C NMR (d$_6$-DMSO) 156.09 (C-6), 152.59 (C-2), 149.71 (C-4), 141.28 (C-8), 118.75 (C-5), 95.42 (CCl$_3$, d, J=8.6), 75.48 (CCl$_3$CH$_2$, d, J=5.7), 70.92 (C-2', d, J=7), 63.99 (C-4', d, J=163), 42.72 (C-1'). IR (KBr) 3372, 3334, 3210, 1658, 1604, 1576. MS (methane/DCI) 536 (100), 534 (50), 192 (95). Anal. Calcd for C$_{12}$H$_{14}$N$_5$O$_{14}$PCl$_6$: C, 26.89; H, 2.63; N, 13.07; Found: C, 26.85; H, 2.55; N, 12.86.

Example 40
PMEA, mono-(2,2,2-trichloroethyl ester)

Mp 218°–225° C. $^1$H NMR (d$_6$-DMSO) 8.51 (2H, s, NH$_2$), 8.30, 8.24 (2H, 2s, H-8, H-2), 4.36 (2H, t, J=5, H-1'), 4.33 (2H, d, J=6, Cl$_3$CCH$_2$), 3.72 (2H, d, J=8, C-4'), 3.91 (2H, t, J=5, H-2'). $^{13}$C NMR (d$_6$-DMSO) 153.03 (C-6), 148.91 (C-2), 148.22 (C-4), 142.78 (C-8), 118.27 (C-5), 97.05 (CCl$_3$), 75.67 (CCl$_3$CH$_2$, d, J=5), 69.99 (C-2', d, J=10), 66.17 (C-4', d, J=159), 43.12 (C-1'). IR (KBr) 3424, 1930, 1690, 1614, 1514, 1414. MS (methane/DCI) 404 (M+H, 1), 136 (40), 113 (100); Anal. Calcd for C$_{10}$H$_{13}$N$_5$O$_4$PCl$_3$.0.3 CCl$_3$CH$_2$OH: C, 28.34; H, 3.05; N, 15.59; Found: C, 28.19; H, 3.17; N, 15.59.

Example 41
PMEA, di-(benzoyloxymethyl ester)

Mp 49°–52° C. $^1$H NMR (d$_6$-DMSO) 8.09 (1H, s, H-8), 7.99 (1H, s, H-2), 7.92 (4H, d, J=7, ArH), 7.67 (2H, t, J=7.5, ArH), 7.49 (2H, t, J=7.5, ArH), 7.18 (2H, s, NH$_2$), 5.82 (4H, d, J=13, OCH$_2$O), 4.22 (2H, t, J=5, H-1'), 4.04 (2H, d, J=8, H-4'), 3.82 (2H, d, J=5, H-2'). $^{13}$C NMR (d$_6$-DMSO) 164.35 (C=O), 156.02 (C-6), 152.45 (C-2), 149.55 (C-4), 140.99 (C-8), 134.22 (ArH), 129.60 (ArH), 128.98 (ArH), 128.35 (ArH), 118.70 (C-5), 70.62 (C-2', d, J=11.5), 64.17 (C-4', d, J=163), 42.29 (C-1'). IR (KBr) 3328, 3182, 1739, 1644, 1602. MS (FAB) 542 (M+H, 45); Anal. Calcd for C$_{24}$H$_{24}$N$_5$O$_6$P.0.66 H$_2$O: C, 52.09; H, 4.61; N, 12.65; Found: C, 52.09; H, 4.36; N, 12.37.

Example 42
PMEA, di-(p-trifluoromethyl benzyl ester)

Mp 115°–125° C. $^1$H NMR (d$_6$-DMSO) 8.18 (1H, s, H-8), 8.17 (1H, s, H-2), 7.66 (4H, d, J=8, ArH), 7.47 (4H, d, J=8, ArH), 7.57 (2H, s, NH$_2$), 5.09 (4H, d, J=8, ArCH$_2$), 4.35 (2H, t, J=5, H-1'), 4.04 (2H, d, J=8, H-4'), 3.91 (2H, t, J=5, H-2'). $^{13}$C NMR (d$_6$-DMSO) 154.99 (C-6), 151.13 (C-2), 149.44 (C-4), 141.7 (C-8), 141.12 (ArC), 128.63 (CF$_3$—ArC, q, J=31.8), 127.93, 125.31 (ArC), 124.17 (CF$_3$, q, J=275), 118.53 (C-5), 70.46 (C-2', d, J=11), 66.14 (ArCH$_2$, d, J=5.5), 63.78 (C-4', d, J=161), 42.61 (C-1'). IR (KBr) 3292, 3118, 1670, 1602, 1476. MS (FAB) 590 (M+H, 100); Anal. Calcd for C$_{24}$H$_{22}$N$_5$O$_4$PF$_6$.0.5 H$_2$O: C, 48.17; H, 3.87; N, 11.70; Found: C, 47.81; H, 3.55; N, 11.30.

Example 43
PMEA, mono-(2,2-difluoro-3-hydroxy propyl ester)

$^1$H NMR (d$_6$-DMSO) 8.20 (2H, s, H-8, H-2), 7.80 (2H, s, NH2), 4.34 (2H, t, J=5.0, H-1'), 4.04 (2H, dt, J=13.2, 7.9), CF$_2$CH$_2$OP), 3.87 (2H, t, J=5.0, H-2'), 3.70 (2H, d, J=8.0, H-4'), 3.60 (2H, t, J=13, HOCH$_2$). $^{13}$C NMR (D$_2$O/NaOD) 157.34 (C-6), 154.24 (C-2), 150.67 (C-4), 144.72 (C-8), 123.54 (CF$_2$, t, J=30), 120.12 (C-5), 72.40 (C-2', d, J=12), 67.75 (C-4', d, J=159), 64.94 (CF$_2$CH$_2$OP, dt, J=30, 5), 63.28 (HOCH$_2$, d, J=27), 45.49 (C-1'). IR (KBr) 3310, 3112, 1694, 1602, 1514. MS (FAB) 368 (M+H, 55). HR-MS (M+H); Anal. Calcd for C$_{11}$H$_{16}$N$_5$O$_5$F$_2$P: 368.0935; Found: 368.0930.

Example 44
PMEA, mono-(p-trifluoromethylbenzyl ester)

$^1$H NMR (d$_6$-DMSO) 8.13 (2H, s, H-8, H-2), 7.69 (2H, d, J=8, ArH), 7.49 (2H, d, J=8, ArH), 7.34 (2H, s, NH$_2$), 4.92 (2H, d, J=8, ArCH$_2$O), 4.32 (2H, t, J=5, C-1'), 3.87 (2H, t, J=5, H-2'), 3.75 (2H, d, J=8, H-4'). IR (KBr) 3062, 1696, 1602, 1514, 1418. MS (FAB) 432 (M+H, 80). HR-MS (M+H); Anal. Calcd for C$_{16}$H$_{17}$N$_5$O$_4$PF$_3$: 432.1048; Found: 432.1039.

Example 45

PMEA, dibutylamide

Mp 117°–119° C. $^1$H NMR (d$_6$-DMSO) 8.12 (2H, s, H-8, H-2), 7.19 (2H, s, NH$_2$), 4.29 (2H, t, J=5, H-1'), 3.82 (2H, t, J=5, H-2'), 3.83 (2H, s, NH), 3.52 (2H, d, J=8, H-4'), 2.64 (4H, m, CH$_2$NH), 1.24 (8H, m, CH$_3$CH$_2$CH$_2$), 0.80 (6H, t, J=7, CH$_3$). $^{13}$C NMR (d$_6$-DMSO) 155.98 (C-6), 152.61 (C-2), 149.71 (C-4), 141.52 (C-8), 118.65 (C-5), 70.46 (C-2', d, J=ll), 67.28 (C-4', d, J=131), 42.83 (C-1'), 39.22 (NHCH$_2$), 34.10 (NHCH$_2$CH$_2$), 19.59 (CH$_3$CH$_2$), 13.92 (CH$_3$). IR 3278, 3242, 2952, 2928, 2872, 1682, 1608. MS (FAB) 384 (M+H, 100); Anal. Calcd for C$_{16}$H$_{30}$N$_7$O$_2$P: C, 50.12; H, 7.89; N, 25.57; Found: C, 49.77; H, 7.79; N, 25.30.

Example 46

PMEA, di(2-methyl-propyl ester)

Mp 109°–110° C. $^1$H NMR(d$_6$-DMSO) 8.10(1H, S, H-8) 8.05(1H, S, H-2), 7.19(2H, S, NH$_2$), 4.31(2H, t, J=5.0, H-1'), 3.87(2H,t,J=5.0,H-2'), 3.85 (2H,d,J=8.5,H-4'), 3.61(4H,dt, J=6.8,1.4,CH$_2$OP), 1.72(2H, apparent heptet, J=6.7,CH), 0.77(12H,d,J=6.7,CH$_3$). $^{13}$C NMR (d$_6$-DMSO) 156.04(C-6), 152.42(C-2), 149.60(C-4), 141.05(C-8), 118.69(C-5), 71.42(CH$_2$OP, d, J=6.7), 70.36(C-2',d,J=11.6), 63.65(C-4', d,J=163), 42.52(C-1'), 28.72(CH,d,J=5.7), 18.45(CH$_3$). IR(KBr) 3286, 3104, 2960, 1670, 1600. MS(FAB) 386(M+ H, 100); Anal. Calcd for C$_{16}$H$_{28}$N$_5$O$_4$P$_1$: C, 49.86; H, 7.32; N, 18.17; Found: C, 49.81; H, 7.26; N, 18.11

Example 47

PMEA, di-(3-methyl-butyl) ester

Mp 94°–98° C. 1H NMR(CDCl$_3$) 8.30(1H, S, H-8) 7.94 (1H, S, H-2), 6.21(2H, S, NH$_2$), 4.37(2H, t, J=5.0, H1'), 4.01(4-H,dt, J=6.8, 6.8, CH$_2$OP), 3.91(2H, t, J=5.0, H-2'), 3.75(2H,d,J=8.0,H-4'), 1.63 (2H, apparent heptet, J=6.6, CH), 1.47(4H,dt, J=6.7, 6.7, CH$_2$CH$_2$OP), 0.84(12H,d,J= 6.5,CH$_3$). $^{13}$C NMR (CDCl$_3$) 155.28(C-6), 152.38(C-2), 150.38(C-4), 141.70(C-8), 119.76(C-5), 71.13(C-2',d,J= 10.0), 65.17(C-4',d,J=166), 65.02(CH$_2$OP,d,J=6.8), 43.46 (C-1'), 39.19(CH$_2$CH$_2$OP,d,J=5.7), 24.50(CH), 22.31(CH$_3$), 22.29(CH$_3$). IR(KBr) 3282, 3106, 2958, 1672, 1600, 1478; MS(methane/DCI) 414(M+H,100); Anal. Calcd. for C$_{18}$H$_{32}$N$_5$O$_4$P$_1$·0.75H$_2$O: C, 50.63; H, 7.91; N, 16.40; Found: C, 50.67; H, 7.66; N, 16.26.

What is claimed is:

1. The compound having formula II

Formula II wherein

B is cytosine or Z;

R$^1$ and R$^2$ are independently OH or OR$^4$ provided that at least one of R$^1$ or R$^2$, is OR$^4$, or one of R$^1$ or R$^2$ is linked to X to form a cyclic compound having Formula V Formula V

* stereochemistry R, S, or RS;

R$^{13}$ is OR$^4$;

X is CH$_2$OR$^6$ (R, S or RS stereochemistry) or hydroxymethyl with the proviso that when X is CH$_2$OR$^6$, then R$^1$ and R$^2$ may additionally be independently chosen from OH;

R$^6$ is a hydrolyzable ester;

R$^4$ is CH$_2$C(O)NR$^5$$_2$, CH$_2$C(O)OR$^5$, CH$_2$OC(O)R$^5$, CH(R$^5$)OC(O)R$^5$(R, S, or RS stereochemistry), CH$_2$C(R$^5$$_2$CH$_2$OH, or CH$_2$OR$^5$; R$^4$ may also be R$^{5'}$;

R$^5$ is C$_1$–C$_{20}$ alkyl, aryl or aryl-alkyl which is unsubstituted or is substituted by hydroxy, oxygen, nitrogen or halogen;

R$^{5'}$ is C$_4$–C$_{20}$ alkyl, aryl or aryl-alkyl which is substituted by hydroxy, oxygen, nitrogen or halogen;

Z is

; and

O is independently H, Cl, NHR$^5$, NR$^5$$_2$, NHC(O)R$^5$, N(C (O)R$^5$)$_2$, OH or NCHN(R$^5$)$_2$ provided that when O is NCHN(R$^5$)$_2$, then R$^5$ is not CH$_3$.

2. A method for the treatment of human cytomegalovirus viral infection in a mammal which comprises administering an antiviral effective non-toxic dose of a compound of claim 1 to the infected mammal for a treatment period of sufficient duration to mitigate said infection provided, however, that B is cytosine and X is hydroxymethyl.

3. The method of claim 2 wherein the compound is administered orally.

4. A pharmaceutical composition which comprises an antiviral effective amount of at least one compound of claim 1 in association with a pharmaceutically acceptable substantially non-toxic carrier or excipient.

5. The compound of claim 1 wherein B is cytosine.

6. The compound of claim 1 wherein R$^{5'}$ is C$_4$–C$_{20}$ alkyl, aryl or aryl-alkyl any one of which is substituted by hydroxy or halogen.

7. The compound of claim 1 wherein R$^{5'}$ is aryl or aryl-alkyl which is unsubstituted or either of which is substituted by substituents independently selected from the group consisting of hydroxy, oxygen, nitrogen and halogen.

* * * * *

UNITED STATES PATENT AND TRADEMARK OFFICE
CERTIFICATE OF CORRECTION

PATENT NO : 5,792,756

DATED : August 11, 1998

INVENTOR(S) : John E. Starrett, Jr., Muzammil M. Mansuri, John C. Martin, David R. Tortolani, Joanne J. Bronson It is certified that error appears in the above-identified patent and that said Letters Patent is hereby corrected as shown below:

In the drawings in Column 5, line 8; and
in the drawings Column 6, line 13, that portion of the formula reading should read Column 28, line 17, change "($R^5{}_2CH_2OH$" to --($R^5$)$_2CH_2OH$--.

Signed and Sealed this

Second Day of May, 2000

Attest:

Q. TODD DICKINSON

*Attesting Officer*     *Director of Patents and Trademarks*